United States Patent [19]

Juby et al.

[11] 4,082,751

[45] Apr. 4, 1978

[54] THERAPEUTIC AGENTS

[75] Inventors: Peter Frederick Juby, Jamesville; Richard Anthony Partyka, Liverpool, both of N.Y.

[73] Assignee: Bristol-Myers Company, New York, N.Y.

[21] Appl. No.: 748,851

[22] Filed: Dec. 8, 1976

Related U.S. Application Data

[63] Continuation-in-part of Ser. No. 657,787, Feb. 13, 1976, abandoned.

[51] Int. Cl.² ............... C07D 403/04; C07D 403/14; A61K 31/505
[52] U.S. Cl. ............... 260/256.4 C; 544/123; 260/256.5 R; 260/256.4 R; 424/248.52; 424/248.53; 424/248.54; 424/248.55; 424/248.56
[58] Field of Search ............... 260/256.5 R, 256.4 C

[56] References Cited

U.S. PATENT DOCUMENTS

| | | | |
|---|---|---|---|
| 3,448,107 | 6/1969 | Hollard | 260/256.4 C |
| 3,660,403 | 5/1972 | Shen et al. | 260/251 R |
| 3,745,161 | 7/1973 | Shen et al. | 260/250 R |
| 3,883,653 | 5/1975 | Barth | 424/251 |

OTHER PUBLICATIONS

Cox et al., Adv. Drug Design 5, 115–196 (1970).
S. Ruheman, Chem. Ber. 30, 821 (1897).
Mitter et al. I, J. Chem. Soc. 123, 2179 (1923).
Mitter et al. II, Quart. J. Indian Chem. Soc. 2, 61 (1925).

*Primary Examiner*—Donald G. Daus
*Assistant Examiner*—Mark L. Berch
*Attorney, Agent, or Firm*—David M. Morse

[57] ABSTRACT

A series of 2-(substituted)phenyl-5-(5-1H-tetrazolyl)-pyrimidin-4(3H)-ones is provided for use as inhibitors of allergic reactions. The compounds show antiallergy activity by both oral and parenteral routes of administration.

39 Claims, No Drawings

THERAPEUTIC AGENTS

CROSS-REFERENCE TO RELATED APPLICATION

This application is a continuation-in-part of co-pending application U.S. Ser. No. 657,787 filed Feb. 13, 1976, now abandoned.

BACKGROUND OF THE INVENTION (1) Field of the Invention

This invention relates to certain 2-phenyl-5-(5-1H-tetrazolyl)pyrimidin-4(3H)-one derivatives and to their use as inhibitors of allergic reactions.

(2) Description of the Prior Art

Various medicinal agents have been employed in the treatment of allergic reactions such as bronchial asthma and allergic rhinitis which are believed to result mainly from antigen-antibody interaction. With respect to bronchial asthma, one of the most serious of these allergically-mediated diseases, bronchodilators such as theophylline, isoproterenol, epinephrine and atropine are used primarily in providing symptomatic relief. These agents, however, have undesirable side effects, e.g. cardiac stimulation and gastrointestinal distress.

With the recent introduction of disodium cromoglycate described by J. S. G. Cox, et al. in Adv. in Drug Res., 5, 115–196 (1970), the physician has been provided with an agent which, when administered to asthmatic patients prior to inhalation of specific antigens, inhibits the release of mediators, e.g. histamine and SRS-A (slow-reacting-substance of anaphylaxis), believed to be responsible for the asthmatic response. While making possible a prophylactic treatment for bronchial asthma without cardiovascular side effects and thus representing a significant advance, disodium cromoglycate suffers from a major disadvantage in that it is not orally absorbed and must be administered by inhalation.

With respect to the 2-phenyl-5-(5-1H-tetrazolyl)-pyrimidin-4(3H)-one derivatives of the present invention, the following references illustrate structurally related compounds known in the art.

1. Preparation of the unsubstituted acid and ester of the formula

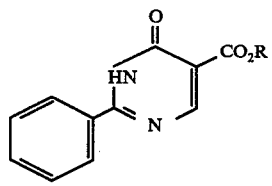

where R is hydrogen or ethyl is disclosed by S. Ruhemann in Ber., 30, 821 (1897).

2. The p-methylphenyl and p-methoxyphenyl substituted esters and acids of the formula

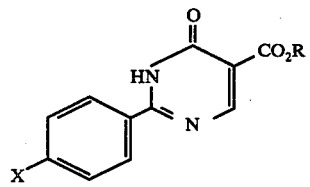

where R is hydrogen or ethyl and X is methyl or methoxy are disclosed by Mitter, et al. in J. Chem. Soc., 123, 2179 (1923) and Quart. J. Indian Chem. Soc., 2, 61 (1925).

3. Shen, et al. in U.S. Pat. Nos. 3,660,403 and 3,745,161 disclose compounds of the general formula

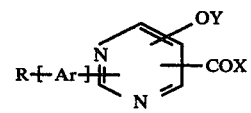

where R—[Ar]— may inter alia be substituted phenyl, Y may be hydrogen and X is any of various substituents including hydroxy, alkoxy or N-heterocyclo. The reference compounds are disclosed as having antiinflammatory, antipyretic and analgesic activity, and no mention is made of any utility as antiallergy agents.

4. U.S. Pat. No. 3,883,643 discloses antiallergy compounds of the formula

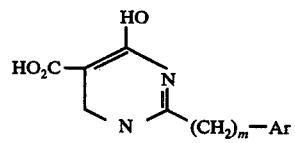

where $m$ is an integer of 0 or 1 and Ar is pyridyl, thienyl, furyl, phenyl or phenyl substituted by hydroxy, methyl, methoxy, nitro, chloro, fluoro, 3,4-dimethoxy, 3,4,5-trimethoxy or alkanoylamino.

5. U.S. Pat. No. 3,448,107 discloses lipid regulating agents of the formula

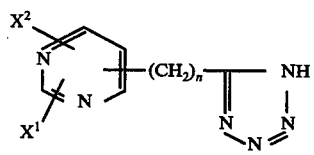

where $X^1$ and $X^2$ may be various substituents including hydroxy, phenyl, p-chlorophenyl, p-methylphenyl and p-aminophenyl and $n$ may be 0 to 4. No disclosure is made of applicants' compounds where in the above formula $n$ is 0 and where the pyrimidinyl ring system is substituted at the 4-position by hydroxy and at the 2-position by substituted phenyl.

SUMMARY OF THE INVENTION

This invention relates to new therapeutically useful 2-(substituted)phenyl-5-(5-1H-tetrazolyl)pyrimidin-4-(3H)-one derivatives, to processes for their preparation, to pharmaceutical compositions containing them and to methods for treating allergically-mediated diseases in mammals by administration of such derivatives or pharmaceutical compositions thereof. The compounds and compositions provided by the present invention are particularly valuable in the prophylactic treatment of allergic bronchial asthma by oral administration.

The antiallergy agents of the present invention may be represented by the formula

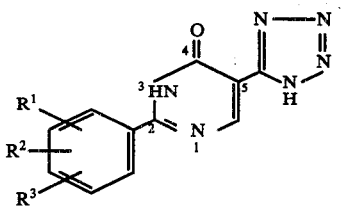

wherein $R^1$, $R^2$ and $R^3$ which may be the same or different are each hydrogen, halogen, (lower)alkyl, (lower)-alkenyl, (lower) alkoxy, —O—(lower)alkenyl,

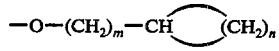

in which $m$ is 0 or an integer from 1 to 6 and $n$ is an integer from 2 to 7, $-OCH_2(CH_2)_xO(CH_2)_yCH_3$ in which $x$ is 0 or an integer from 1 to 6 and $y$ is 0 or an integer from 1 to 6, $CF_3$, $-OCF_3$, $-OCH_2CF_3$, hydroxy, (lower)alkylthio, amino, nitro,

in which $r$ is 4 or 5,

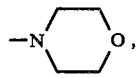

(lower)alkylamino, di(lower)alkylamino, carboxyl, $-CO_2-$ (lower)alkyl, $-O(CH_2)_uCO_2R^a$ in which $u$ is an integer from 1 to 6 and $R^a$ is hydrogen or (lower)alkyl, acyl, acylamino, acyloxy,

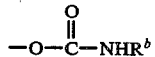

in which $R^b$ is (lower)alkyl, $-O(CH_2)_kOH$ in which $k$ is an integer from 2 to 6,

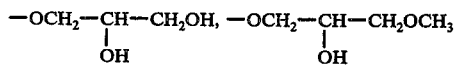

or $-OCH_2C_6H_5$, and pharmaceutically acceptable salts thereof, with the proviso that $R^1$, $R^2$ and $R^3$ may not all be alike except in the case where they represent (lower)-alkoxy.

The $R^1$, $R^2$ and $R^3$ substituents mentioned above may be located at any of the available positions of the phenyl ring, i.e. at the 2-6 positions. The substituents may be alike or different, but the only compounds included within the scope of the invention where $R^1=R^2=R^3$ are those in which $R^1$, $R^2$ and $R^3$ are all (lower)alkoxy. The substituent groups disclosed above may be further defined as follows:

(a) Halogen includes chlorine, bromine, fluorine and iodine. Preferred halogen substituents are chlorine and fluorine;

(b) (Lower)alkyl includes both straight and branched chain saturated aliphatic hydrocarbon radicals having from 1-10 carbon atoms inclusive, e.g. methyl, ethyl, n-propyl, isopropyl, n-butyl, isobutyl, sec-butyl, tert-butyl, n-pentyl, isopentyl, n-hexyl, n-heptyl, n-octyl, n-nonyl and n-decyl. Preferred substituents are those having from 1-6 carbon atoms and most preferred are $C_1$-$C_4$ alkyl radicals;

(c) (Lower)alkenyl includes straight or branched chain unsaturated aliphatic hydrocarbon radicals containing one double bond and having from 2-10 carbon atoms inclusive, e.g. vinyl, allyl, isopropenyl, 2- or 3-methallyl or 3-butenyl. Preferred groups are $C_2$-$C_6$ alkenyl radicals;

(d) (Lower)alkoxy includes $C_1$-$C_{10}$ alkoxy radicals, the alkyl portion of such radicals being defined as in (b) above. Examples include methoxy, ethoxy, n-propoxy, isopropoxy, n-butoxy, isobutoxy, sec-butoxy, n-pentyloxy, isopentyloxy, n-hexyloxy, etc. Preferred groups are $C_1$-$C_6$ alkoxy and most preferred are $C_1$-$C_4$ alkoxy radicals;

(e) —O—(lower)alkenyl groups include radicals in which the alkenyl portion is as defined above in (c), e.g. vinyloxy, allyloxy or isopropenyloxy. A most preferred group is allyloxy;

(f)

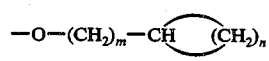

includes cyclo(lower)alkoxy and cyclo(lower)alkyl-($C_1$-$C_6$) alkyloxy group in which the cycloalkyl ring contains from 3 to 8 carbon atoms, preferably 3-6 carbon atoms. Examples of such groups are cyclopropyloxy, cyclobutyloxy, cyclopentyloxy, cyclohexyloxy, cycloheptyloxy, cyclopropylmethyloxy, cyclopropylethyloxy, cyclobutylmethyloxy, cyclobutylethyloxy, cyclopentylmethyloxy, cyclohexylmethyloxy, cyclohexylethyloxy and cyclohexylpropyloxy;

(g) $-O-CH_2(CH_2)_xO(CH_2)_yCH_3$ includes radicals such as $-OCH_2OCH_3$, $-OCH_2CH_2OCH_3$, $-OCH_2CH_2OCH_2CH_3$, $-OCH_2OCH_2CH_3$ and $-OCH_2CH_2CH_2OCH_2CH_3$;

(h) (Lower)alkylthio includes $C_1$-$C_{10}$ alkylthio radicals in which the alkyl portion is as defined above in (b). Examples of such groups are methylthio, ethylthio, propylthio and butylthio;

(i) (Lower)alkylamino includes $C_1$-$C_{10}$ alkylamino radicals in which alkyl is as defined as in (b). Examples of such groups are methylamino, ethylamino, propylamino and butylamino;

(j) Di(lower)alkylamino includes di $C_1$-$C_{10}$ alkylamino radicals in which alkyl is as defined above in (b). Examples of such groups are dimethylamino and diethylamino;

(k) $-CO_2-$(lower)alkyl includes ester radicals in which the alkyl moiety is as defined above in (b), e.g. carbomethoxy, carbethoxy, carbopropoxy and carbobutoxy.

(l) $-O(CH_2)_uCO_2R^a$ represents radicals in which $R^a$ is as defined in (b) above such as $-OCH_2CO_2H$, $-OCH_2CH_2CO_2H$, $-OCH_2CH_2CH_2CO_2H$, $-OCH_2CO_2CH_3$, $-OCH_2CO_2C_2H_5$, $-OCH_2CH_2CO_2CH_3$ and $-OCH_2CH_2CO_2C_2H_5$;

(m) Acyl includes radicals of the type $R^c-CO-$ where $R^c$ is an aliphatic, cycloaliphatic, aromatic or araliphatic hydrocarbon radical or a heterocyclic or heterocyclic-aliphatic radical, e.g. $CH_3CO-$, $C_2H_5CO-$, $C_3H_7CO-$, $C_6H_5CO-$, $C_6H_5CH_2CO-$,

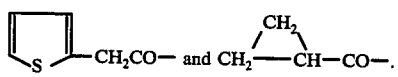

Preferred acyl groups are those in which $R^c$ is alkyl as defined in (b);

(n) Acylamino includes radicals of the type $R^c-CO-NH-$ where $R^c$ is as defined above in connection with acyl and is preferably $C_1-C_{10}$ alkyl. Examples of such groups are $CH_3CONH-$, $C_2H_5CONH-$ and $C_6H_5CONH-$;

(o) Acyloxy includes radicals of the type $R^c-COO-$ in which $R^c$ is as defined above in connection with acyl and is preferably $C_1-C_{10}$ alkyl. Examples are $CH_3COO-$, $C_2H_5COO-$, $C_3H_7COO-$, $C_6H_5CH_2COO-$ and $C_6H_5COO-$;

(p)

includes pyrrolidino and piperidino; and (q)

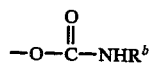

includes (lower)alkyl carbamoyloxy radicals in which the (lower)alkyl portion is as defined above in (b). Examples of such substituents include $-OCONHCH_3$, $-OCONHC_2H_5$ and $-OCONHC_3H_7$.

A preferred embodiment of the present invention comprises the compounds of the formula

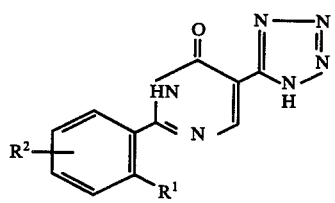

wherein $R^1$ and $R^2$ which may be the same or different are as defined above in connection with the compounds of general formula I, with the proviso that $R^1$ may never be hydrogen, and the pharmaceutically acceptable salts of said compounds of formula I'.

Preferred compounds and salts of formula I' are those in which $R^1$ is (lower)alkoxy, i.e. straight or branched chain $C_1-C_{10}$ alkoxy, $-O-$(lower)alkenyl or

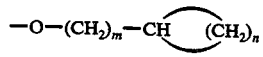

in which m is 0 or an integer from 1 to 6 and n is an integer from 2 to 7. Within this group, preferred subgroups are those compounds and salts of formula I' in which:

(a) $R^1$ is $-O-C_1-C_6$ alkyl, most preferably methoxy, ethoxy, n-propoxy, isopropoxy, n-butoxy, isobutoxy or sec-butoxy;

(b) $R^1$ is $-O-C_2-C_6$ alkenyl, most preferably allyloxy; and (c) $R^1$ is

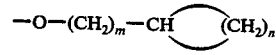

in which m is 0 or an integer from 1 to 4 and n is an integer from 2 to 5, most preferably cyclopropylmethoxy. The preferred $R^2$ substituents for the compounds of formula I' are hydrogen, (lower)alkoxy, $-O-$(lower)alkenyl,

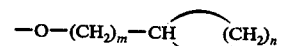

in which m is 0 or an integer from 1 to 6 and n is an integer from 2 to 7, nitro, amino or di(lower)alkylamino. Most preferred $R^2$ substituents are hydrogen, (lower)alkoxy, nitro, amino or di(lower)alkylamino.

A more preferred embodiment of the present invention comprises the compounds of the formula

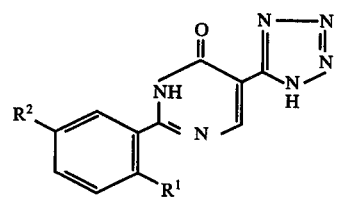

wherein $R^1$ and $R^2$ which may be the same or different are as defined above in connection with the compounds of general formula I, with the proviso that $R^1$ is never hydrogen, and the pharmaceutically acceptable salts of said compounds of formula I''.

Preferred compounds and salts of formula I'' are those in which $R^1$ is (lower)alkoxy, $-O-$(lower)alkenyl or

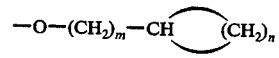

in which m is 0 or an integer from 1 to 6 and n is an integer from 2 to 7. Within this group, preferred subgroups are those compounds and salts of formula I'' in which:

(a) $R^1$ is $-O-C_1-C_6$ alkyl, most preferably methoxy, ethoxy, n-propoxy, isopropoxy, n-butoxy, isobutoxy or sec-butoxy;

(b) $R^1$ is $-O-C_2-C_6$ alkenyl, most preferably allyloxy; and (c) $R^1$ is

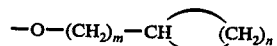

in which m is 0 or an integer from 1 to 4 and n is an integer from 2 to 5, most preferably cyclopropylmethoxy. The preferred $R^2$ substituents for the compounds of formula I'' are hydrogen, (lower)alkoxy, $-O-$(lower)alkenyl,

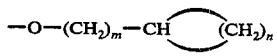

in which m is 0 or an integer from 1 to 6 and n is an integer from 2 to 7, nitro, amino or di(lower)alkylamino. Most preferred R² substituents are hydrogen, (lower)alkoxy, nitro, amino or di(lower)alkylamino.

Particularly preferred compounds and salts of formula I'' are those in which R¹ is methoxy, ethoxy, n-propoxy, isopropoxy, n-butoxy, isobutoxy, sec-butoxy, allyloxy or cyclopropylmethoxy and R² is methoxy, ethoxy, n-propoxy, isopropoxy, n-butoxy, isobutoxy, sec-butoxy, allyloxy, cyclopropylmethoxy, nitro, amino or dimethylamino.

Another more preferred embodiment of the present invention comprises the compounds of the formula

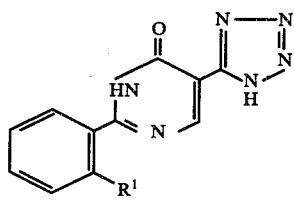

I''' wherein R¹ is halogen, (lower)alkyl, (lower)alkenyl, (lower)alkoxy, —O—(lower)alkenyl,

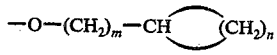

in which m is 0 or an integer from 1 to 6 and n is an integer from 2 to 7, —OCH₂(CH₂)ₓO(CH₂)ᵧCH₃ in which x is 0 or an integer from 1 to 6 and y is 0 or an integer from 1 to 6, CF₃, —OCF₃, —OCH₂CF₃, hydroxy, (lower)alkylthio, amino,

in which r is 4 or 5,

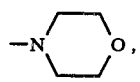

(lower)alkylamino, di(lower)alkylamino, carboxyl, —CO₂—(lower)alkyl, —O(CH₂)ᵤCO₂Rᵃ in which u is an integer from 1 to 6 and Rᵃ is hydrogen or (lower)alkyl, acyl (preferably Rᶜ—CO— in which Rᶜ is (lower)alkyl), acylamino (preferably Rᶜ—CO—NH— in which Rᶜ is (lower)alkyl), acyloxy (preferably Rᶜ—COO— in which Rᶜ is (lower)alkyl),

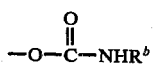

in which Rᵇ is (lower)alkyl, —O(CH₂)ₖOH in which k is an integer from 2 to 6,

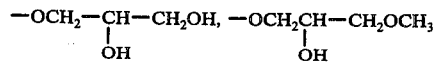

or —OCH₂C₆H₅, and pharmaceutically acceptable salts thereof.

A preferred group of compounds within the scope of formula I''' comprises those compounds of formula I''' wherein R¹ is (lower)alkoxy, —O—(lower)alkenyl,

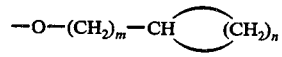

in which m is 0 or an integer from 1 to 6 and n is an integer from 2 to 7, —OCH₂(CH₂)ₓO(CH₂)ᵧCH₃ in which x is 0 or an integer from 1 to 6 and y is 0 or an integer from 1 to 6, —OCF₃, —OCH₂CF₃, hydroxy, (lower)alkylthio, amino, (lower)alkylamino, di(lower)alkylamino, —O(CH₂)ᵤCO₂Rᵃ in which u is an integer from 1 to 6 and Rᵃ is hydrogen or (lower)alkyl, —O(CH₂)ₖOH in which k is an integer from 2 to 6,

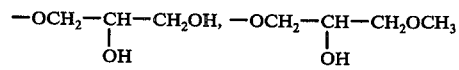

or —OCH₂C₆H₅, or a pharmaceutically acceptable salt thereof. Within this group, those compounds wherein R¹ is (lower)alkoxy, —O—(lower)alkenyl,

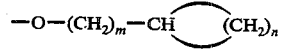

in which m is 0 or an integer from 1 to 6 and n is an integer from 2 to 7, —OCH₂(CH₂)ₓO(CH₂)ᵧCH₃ in which x is 0 or an integer from 1 to 6 and y is 0 or an integer from 1 to 6, —OCF₃, —OCH₂CF₃, hydroxy, —O(CH₂)ᵤCO₂Rᵃ in which u is an integer from 1 to 6 and Rᵃ is hydrogen or (lower)alkyl, —O(CH₂)ₖOH in which k is an integer from 2 to 6,

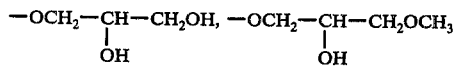

or —OCH₂C₆H₅, or pharmaceutically acceptable salts thereof, are preferred.

Other preferred compounds and salts of formula I''' are those in which R¹ is (lower)alkoxy, —O—(lower)alkenyl or

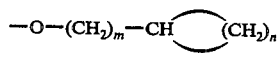

in which m is 0 or an integer from 1 to 6 and n is an integer from 2 to 7.

More preferred compounds and salts of formula I''' are those in which R¹ is —O—C₁—C₆ alkyl, most preferably methoxy, ethoxy, n-propoxy, isoproproxy, n-butoxy, isobutoxy, or sec-butoxy; —O—C₂—C₆ alkenyl, most preferably allyloxy; or

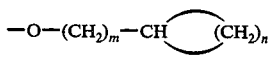

in which m is 0 or an integer from 1 to 4 and n is an integar from 2 to 5, most preferably cyclopropylmethoxy.

Most preferred compounds and salts of formula I''' are those in which $R^1$ is methoxy, ethoxy, n-propoxy, isopropoxy, n-butoxy, isobutoxy, sec-butoxy, allyloxy or cyclopropylmethoxy.

Since the compounds of this invention are amphoteric in nature, they can be converted to salts of either acids or bases by treating said compounds with a substantially equimolar amount of a chosen acid or base in an aqueous solution or in a suitable organic solvent such as methanol or ethanol. When such salts are to be used for human consumption, the acids or bases which are used to prepare the pharmaceutically acceptable salts must, of course, be those which necessarily form non-toxic salts. Examples of suitable acids include hydrochloric, hydrobromic, hydroiodic, nitric, sulfuric, phosphoric, acetic, lactic, citric, tartaric, oxalic, succinic, maleic, gluconic, ascorbic and p-toluene sulfonic. Pharmaceutically acceptable salts may be formed from such bases as ammonia, organic amines and metal salts, e.g. metal salts containing sodium, potassium, calcium, magnesium, barium and aluminum cations. Representative of such bases are ammonia, primary amines such as n-propylamine, n-butylamine, ethanolamine, ethylenediamine, cyclohexylamine, benzylamine, ethylamine, octylamine or tris(hydroxymethyl)aminomethane, secondary amines such as diethanolamine, tertiary amines such as triethanolamine, N-methylpyrrolidine, N-methylmorpholine or 1,5-diazabicyclo-[4,3,0]-5-nonene and metal compounds such as sodium hydroxide, potassium hydroxide, ammonium hydroxide, sodium ethoxide, potassium methoxide, magnesium hydroxide, calcium hydroxide or aluminum hydroxide.

Those skilled in the art will appreciate that the compounds represented by formula I contain two tautomeric hydrogen atoms, and the compounds are thus capable of existing in the forms 1-6 shown below. All the forms may be present to a greater or lesser degree and are in a state of dynamic equilibrium with each other. This invention embraces all such forms, but for the sake of convenience structure 1 has been arbitrarily used herein to describe the present compounds.

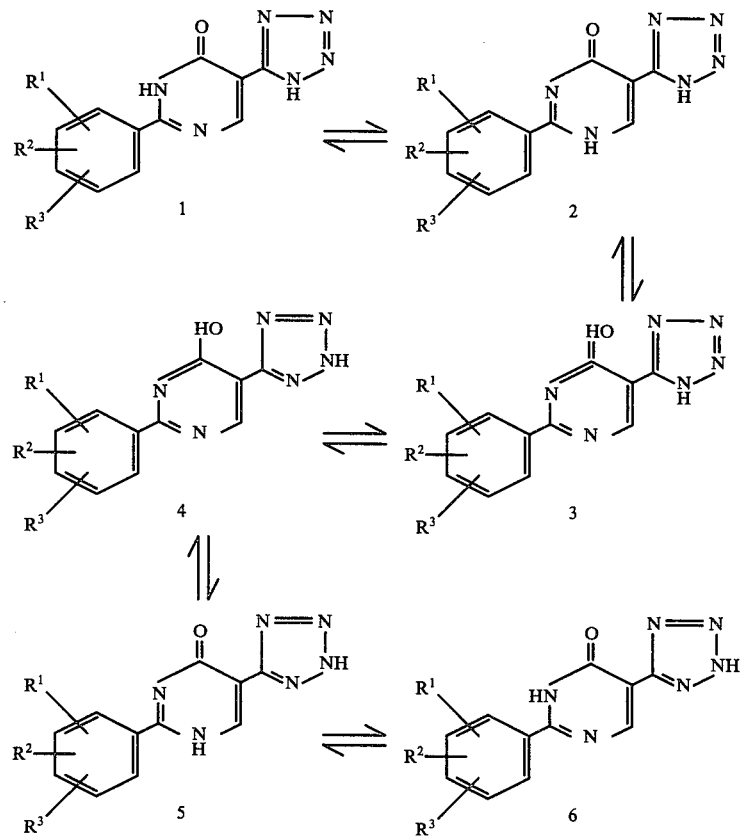

The compounds of the present invention may be prepared by several alternative methods. One preferred method is disclosed by W. G. Finnegan, et al. in J. Am. Chem. Soc., 80, 3908 (1958) and comprises reacting and appropriate nitrile of the formula

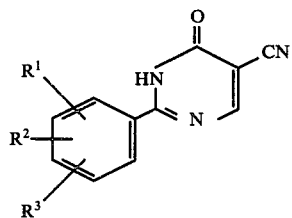

II (wherein R¹, R² and R³ are defined as above in reference to formula I) with an azide salt selected from the group consisting of ammonium, substituted ammonium, sodium and lithium azide in an inert organic solvent. The nitrile II and azide salt may be used in approximately equimolar amounts. Examples of suitable azide salts are provided by Finnegan in the above-mentioned reference and include azides such as $NaN_3$, $LiN_3$, $NH_4N_3$, $(n-C_4H_9)_2NH_2N_3$, $C_6H_5NH_3N_3$, and $(CH_3)_4NN_3$. The azide salt may be added directly or may be generated in situ, e.g. by double decomposition reactions of sodium azide and an appropriate chloride salt such as LiCl, $NH_4Cl$, $(CH_3)_4NCl$, etc. While the condensation reaction proceeds over a wide temperature range, it is preferred in order to minimize reaction times to use elevated temperatures, e.g. from about 100° C up to the reflux temperature of the solvent system. The inert organic solvent may in general be any solvent having good solvent power for the azide salt and which is chemically inert. Examples of preferred solvents are dimethylformamide, dimethylacetamide, dimethylsulfoxide and hexamethylphosphoramide. The most preferred solvent is dimethylformamide. The condensation reaction is found to be subject to general acid catalyst and yields are improved by addition of such reagents as hydrazoic acid, amine hydroazides and Lewis acids such as $BF_3$ to the sodium azide. At the completion of the reaction, the tetrazole product may be recovered from the reaction mixture by removing the solvent, diluting the residue with water and then acidifying the mixture to give the desired compound of formula I. The product may be further purified by recrystallization, e.g. from glacial acetic acid, and optionally converted to a pharmaceutically acceptable salt thereof as described above. Following condensation, products of formula I may if desired be further reacted by methods known per se to convert one or more R¹, R², or R³ substituent groups to other substituent groups within the scope of formula I. Thus, for example, a compound of formula I where R¹, R² or R³ is nitro may be subjected to catalytic hydrogenation to give the corresponding amino-substituted compound or a compound where R¹, R² or R³ is amino may be alkylated to give the corresponding (lower)alkylamino- or di(lower)-alkylamino-substituted compound.

An alternative variation of the above procedure involves condensing the nitrile starting material II with aluminium azide in tetrahydrofuran followed by an acidification recovery step as described above. The reaction may conveniently be carried out by reacting nitrile II with aluminum chloride and sodium azide in molar proportions of about 1:1:3, respectively. While the temperature for the reaction is not critical, advantageous results have been obtained at reflux temperature.

Another alternative method for preparing the compounds of formula I comprises heating the desired nitrile compound of formula II with either hydrazoic acid in an inert organic solvent such as benzene, xylene or toluene or with sodium azide and acetic acid in butanol. In this procedure an acidification step is not required to recover the desired end-product.

Yet another alternative and preferred procedure for preparing the compounds of formula I comprises reacting an acrylate intermediate of the formula

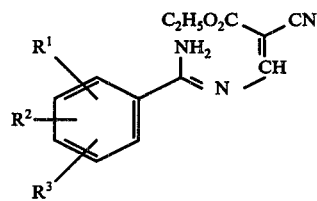

(wherein R¹, R² and R³ are as defined above in reference to Formula I) with sodium azide and ammonium chloride in an inert organic solvent. The preferred reaction conditions, i.e. molar ratios, temperature range and solvents, are described above in connection with the $NaN_3/NH_4Cl$ condensation procedure. The product of formula I may be conveniently recovered from the reaction mixture by addition of sufficient water followed by acidification to effect precipitation of the desired compound I.

A most preferred procedure for preparing the compounds of formula I comprises reacting a substituted benzamidine of the formula

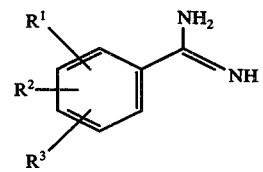

(wherein R¹, R² and R³ are as defined above in reference to formula I) and ethyl ethoxymethylene cyanoacetate of the formula $C_2H_5OCH\!\!=\!\!C(CN)CO_2C_2H_5$ in an inert organic solvent with sodium azide and ammonium chloride. Approximately equimolar quantities of the four reactants are used in an organic solvent which is reaction-inert and which possesses good solvent power for the sodium azide. Suitable solvents include dimethylformamide, dimethylacetamide, dimethylsulfoxide and hexamethylphosphoramide. The most preferred solvent is dimethylformamide. For best results the reaction is carried out with heating, preferably at temperatures from about 100° C. up to the reflux temperature of the solvent system. At the conclusion of the reaction, the desired product can be recovered by addition of sufficient water followed by acidification to precipitate compound I from the reaction mixture.

The above process is a most preferred embodiment of the present invention since it enables compound I to be prepared directly from the basic benzamidine and ethyl ethoxymethylenecyanoacetate starting materials in one step without the necessity of first preparing and isolating one or more intermediates required for the alternative methods described above. The advantages in overall yield and simplicity of operation will be apparent from examining the illustrative examples below.

The nitrile starting materials of formula II may be prepared by various known reaction routes. One preferred method [J. Heterocycl. Chem., 8, 715-719(1971)] involves dehydration as with phosphorus oxychloride of the corresponding amide of formula III according to the following reaction sequence:

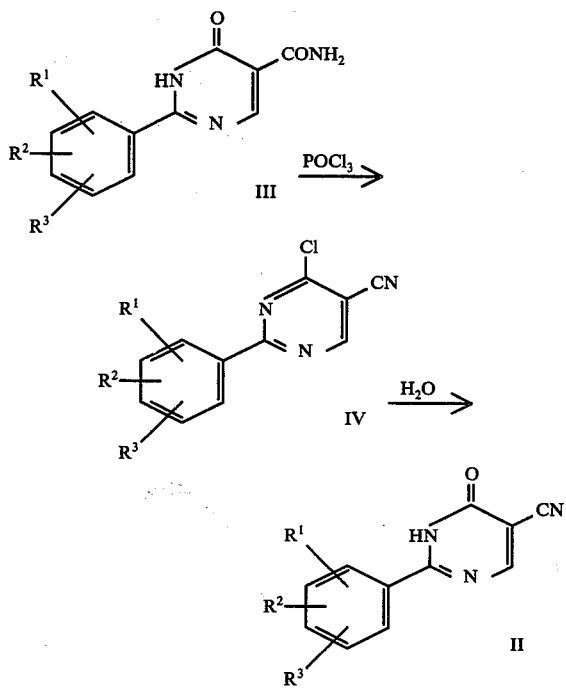

The dehydration step is accomplished at elevated temperatures, most preferably under reflux conditions.

Amide compounds of formula III may be obtained by treatment of the corresponding esters of the formula

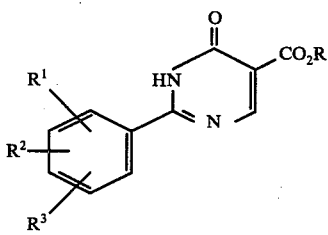

wherein R is $C_1$-$C_6$ alkyl with liquid ammonia, ammonium hydroxide or a solution of ammonia in a (lower)alkanol (e.g. methanol or ethanol) containing an excess of sodium methoxide. The reaction is conveniently carried out in a sealed vessel at steam bath temperature. When concentrated ammonium hydroxide is used, good results have also been achieved by reaction at room temperature for two to three days without the necessity of either heat or a sealed vessel.

The ester intermediates of formula V may be prepared by condensation of a substituted benzamidine of the formula

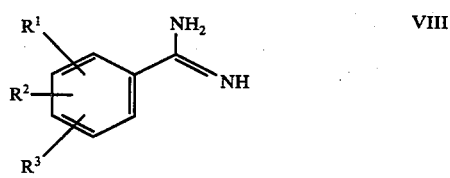

where $R^1$, $R^2$ and $R^3$ are as defined above (in connection with compounds of formula I), or an acid addition salt thereof, with a compound of the formula

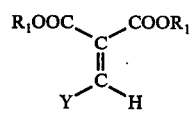

wherein $R_1$ is $C_1$-$C_6$ alkyl and Y is a suitable leaving group such as $-OC_2H_5$, $-CH(COOC_2H_5)_2$,

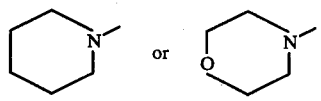

in an inert organic solvent and in the presence of a condensing agent.

The condensation of reactants VII and VIII is carried out in an inert organic solvent, e.g., a $C_1$-$C_6$ alcohol, acetonitrile or tetrahydrofuran, and, advantageously, at elevated temperatures. Good results have been obtained when the reactants are refluxed in ethanol.

Compounds VII and VIII are generally reacted together in the presence of from at least a catalytic amount up to a several-fold molar excess of a suitable condensing agent. Alkali metal alkoxides (commonly prepared in situ by addition of the alkali metal to a $C_1$-$C_6$ alcohol) such as sodium methoxide are preferred condensing agents. When the benzamidine or benzamidine salt is condensed with diethyl ethoxymethylenemalonate, the alkali metal alkoxide condensing agent may be replaced by alkali metal carbonates or may even be eliminated as shown in the examples below.

Benzamidine starting material VII may be used either as the free base or as a salt thereof, e.g. the hydrochloride, fluorosulfonate or methyl sulfate salts. When the free base is employed, a molar equivalent or slight excess thereof of the alkali metal alkoxide is preferably used. If a benzamidine salt is used, two moles of alkoxide per mole of compound VII are found to provide advantageous results. A preferred condensation procedure involves condensing the benzamidine or benzamidine salt (e.g. the methyl sulfate) with diethyl ethoxymethylenemalonate in an inert organic solvent (preferably ethanol) in the presence of about one mole of potassium carbonate per mole of benzamidine or salt thereof with heating, preferably at reflux temperature. Good results have also been obtained in the above procedure when the benzamidine free base is condensed with the diethyl ethoxymethylenemalonate in the absence of a condensing agent.

Compounds VII and VIII are employed in approximately equimolar amounts. Schemes I-III below illustrate condensation reaction procedures which are embodiments of the general process described above.

Scheme I

A substituted benzamidine may be condensed with an alkyl dicarboxyglutaconate by the general method of S. Ruhemann in Ber. 30, 821 (1897). Illustrative of this procedure is the reaction

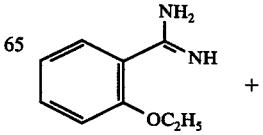

+

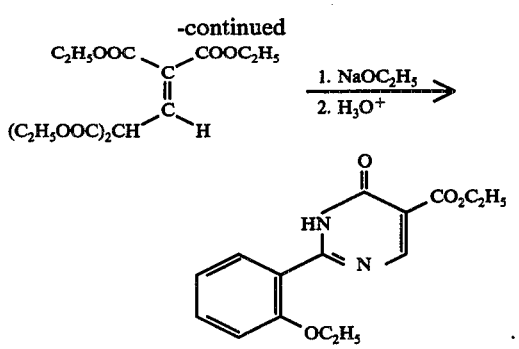

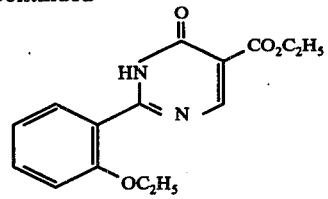

Scheme II

The substituted benzamidine VII is reacted with a dialkyl ethoxymethylenemalonate according to the general method described by P. C. Mitter, et al. in J. Chem. Soc., 123, 2179 (1923) and Quart. J. Indian Chem. Soc., 2, 61–70 (1925). Typifying this procedure is the sequence

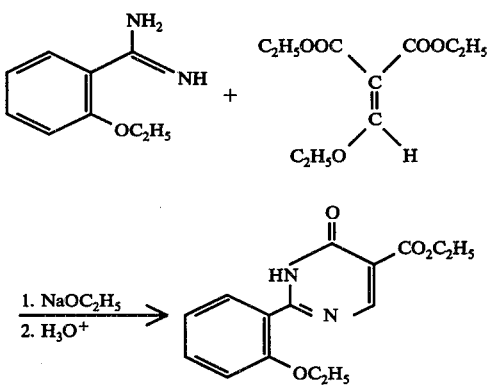

Reaction scheme II is illustrative of the preferred process for preparing the intermediates V of the present invention. As described above another preferred procedure involves the reaction

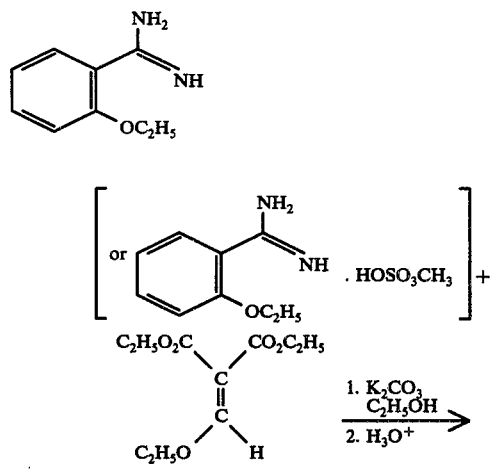

Scheme III

A third condensation procedure described by Santilli, et al. in J. Med. Chem., 7, 68 (1964) involves condensing the benzamidine with a dialkyl morpholinomethylenemalonate or a dialkyl piperidinomethylenemalonate. An example of this procedure is the reaction

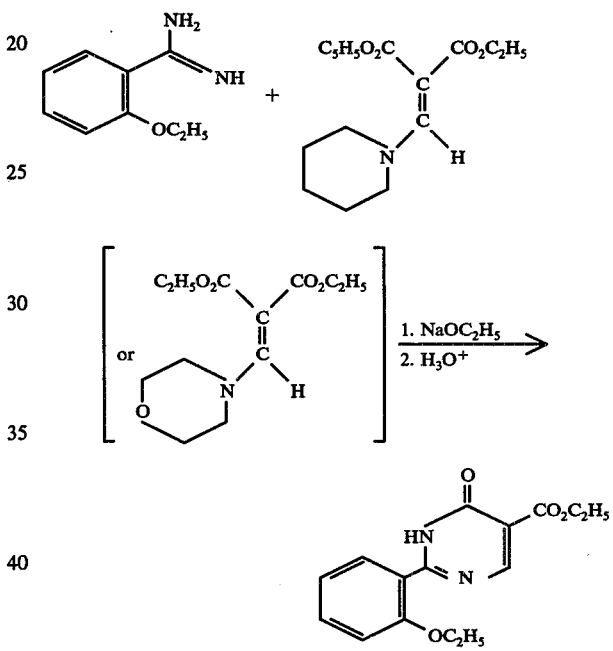

Use of an alkali metal condensing agent, e.g. $K_2CO_3$ or $NaOC_2H_5$, in the above procedures results in formation of a soluble alkali metal salt. Acidification of the reaction mixture with a mineral acid or an organic acid such as acetic acid will cause the desired ester to precipitate out of solution.

Starting materials VII and VIII are either known or are prepared by methods known in the art. A preferred method of preparation of substituted benzamidines VII may be represented by the reaction sequence (illustrated for the case where $R^1 = -OC_2H_5$ and $R^2 = R^3 = H$)

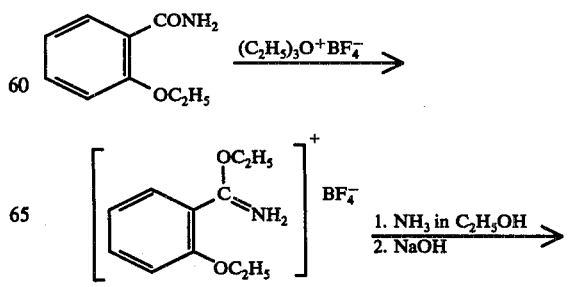

-continued

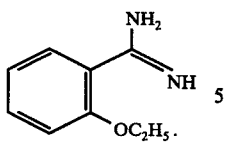

In this procedure which is described in U.S. Pat. No. 3,819,631 and J. Org. Chem., 33, 1679 (1968), the triethyloxonium fluoroborate reactant mentioned above may be replaced by alkyl fluorosulfonates (e.g. methyl fluorosulfonate), dimethyl sulfate or by other alkyloxonium fluoroborates. A most preferred procedure involves use of the relatively inexpensive dimethyl sulfate [$(CH_3O)_2SO_2$] as the alkylating agent in place of the more costly alkyl fluorosulfonates and triethyloxonium fluoroborate. This procedure which is outlined below results in formation of a benzamidine methyl sulfate salt.

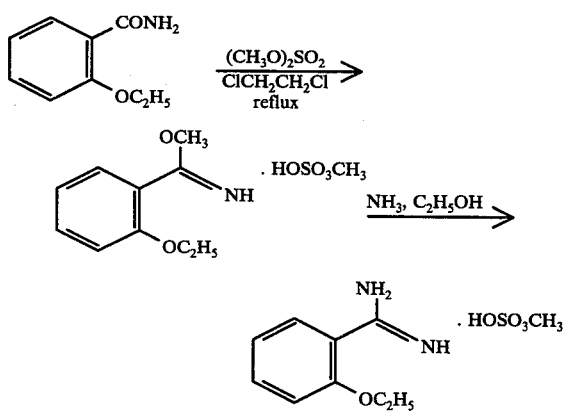

An alternative procedure for preparing benzamidine compounds of formula VII comprises the reaction (illustrated for the case where $R^1 = -OC_2H_5$ and $R^2 = R^3 = H$)

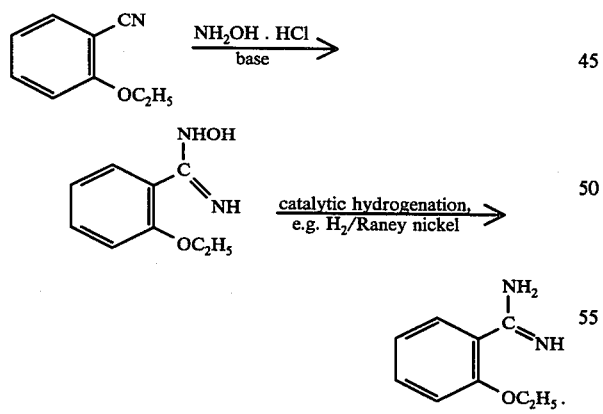

An alternative method for preparing the nitriles of formula II comprises (a) condensing a substituted benzamidine VII with an equimolar amount of ethoxymethylene cyanoacetate of the formula

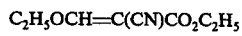

in an inert organic solvent, e.g. a $C_1$-$C_6$ alcohol (preferably ethanol) or dimethylformamide, preferably with cooling to temperatures of about 0° C., to produce an acrylate intermediate VI of the formula

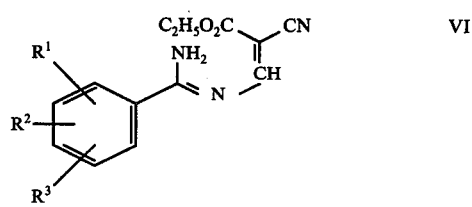

and (b) cyclizing intermediate VI by heating (at temperatures ranging from slightly above room temperature to the reflux temperature of the solvent) in an inert organic solvent, e.g. dimethylsulfoxide, toluene or dimethylformamide, to produce the desired nitrile II. The general process of preparting the intermediates of formula VI is disclosed by Nishigaki et al. in Chem. Pharm. Bull., 18, 1003 (1970) for the case in which $R^1$, $R^2$ and $R^3$ are all hydrogen.

The above-mentioned process has been found to be much superior to the base catalyzed condensation of benzamidines with ethyl ethoxymethylenecyanoacetate described in Quart. J. Indian Chem. Soc., 2, 61 (1925) and in U.S. Pat. No. 3,660,403 which produces a mixture of both the desired nitrile II and the unwanted amino ester of the formula

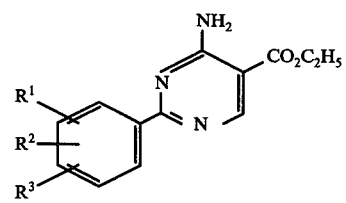

The acrylate intermediate VI produced above may also be converted directly to the desired product of formula I by reaction with sodium azide and ammonium chloride in an inert organic solvent.

A still further method which can be used for preparation of the nitrile compounds of formula II is disclosed by Hromatka in U.S. Pat. No. 2,235,638. The Hromatka procedure involves the reaction sequence

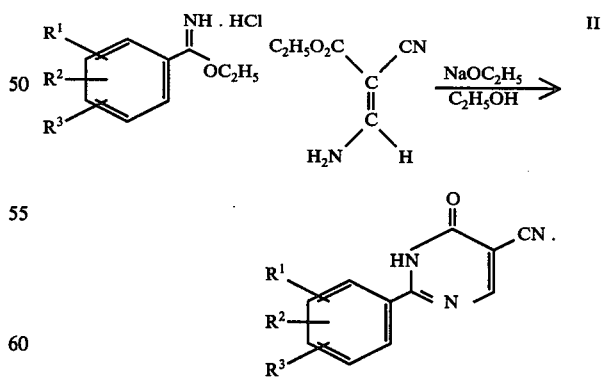

In preparing compounds of formula I in which $R^1$, $R^2$ or $R^3$ contain free hydroxy, amino or carboxyl groups, it is of course understood that such groups will be protected by suitable known protecting groups during the reaction steps beginning with the benzamide starting materials through the formation of the final tetrazoles. The protecting group(s) may then be removed by methods known per se to give the desired products having the unprotected substituent groups. In preparing compounds of formula I where $R^1$, $R^2$ or $R^3$ are (lower)alkylamino or di(lower)alkylamino, the corresponding amino-substitued compound may first be prepared and then alkylated by methods known per se. Alternatively, the dialkylamino-substituted compounds can be prepared directly from the appropriate benzamide starting material.

As noted previously, the compounds of formula I have been found to inhibit the release of toxic products, i.e. mediators, which arise from the combination of certain types of antibody and specific antigen. They are of particular value in preventing the symptoms of allergic bronchial asthma in mammalian subjects by administering to such subject a mediator-inhibiting dose of a compound of formula I. The componds may also be useful for the relief and prophylaxis or other allergic reactions such as allergic rhinitis.

The compounds of the present invention may be administered either as individual therapeutic agents or as mixtures with other therapeutic agents. They may be administered alone but are generally administered in the form of pharmaceutical compositions, i.e. mixtures of the active agents with suitable pharmaceutical carriers or diluents. Examples of such compositions include tablets, lozenges, capsules, powders, aerosol sprays, aqueous or oily suspensions, syrups, elixers and aqueous solutions for injection. The compounds are most preferably administered in oral dosage forms.

The nature of the pharmaceutical composition and the pharmaceutical carrier or diluent will, or course, depend on the desired route of administration, i.e. orally, parenterally or by inhalation. Oral compositions may be in the form of tablets or capsules and may contain conventional excipients such as binding agents (e.g. syrup, acacia, gelatin, sorbitol, tragacanth or polyvinylpyrrolidone), fillers (e.g. lactose, sugar, maize-starch, calcium phosphate, sorbitol or glycine), lubricants (e.g. magnesium stearate, talc, polyethylene glycol, or silica), disintegrants (e.g. starch) or wetting agents (e.g. sodium lauryl sulfate). Oral liquid preparations may be in the form of aqueous or oily suspensions, solutions, emulsions, syrups, elixers, etc. or may be presented as a dry product for reconstitution with water or other suitable vehicle before use. Such liquid preparations may contain conventional additives such as suspending agents, flavoring agents, diluents or emulsifying agents. For parenteral administration or inhalation, solutions or suspensions of a compond of formula I with conventional pharmaceutical vehicles may be employed, e.g. as an aerosol spray for inhalation, as an aqueous solution for intravenous injection or as an oily suspension for intramuscular injection. The compounds may also be administered by means of inhalers or other devices which permit the active compounds in the form of dry powders to come into direct contact with the lungs.

The compounds of the present invention or pharmaceutical compositions thereof may be administered to human asthmatic patients in single oral doses of approximately 1-500 mg. of active ingredient and multiple oral doses totalling up to about 1000 mg./day of active ingredient. When administered by inhalation, lower doses are generally given, i.e. on the order of about 0.1 of the normal oral dosage for the particular compound in question. These values are illustrative only, however, and the physician of course will ultimately determine the dosage most suitable for a particular patient on the basis of factors such as age, weight, severity of the symptoms and the particular agent to be administered.

The in vivo animal model studies described below indicate that the compounds of formula I are highly potent antiallergy agents.

Biological Activity Data

The reagin-mediated rat Passive Cutaneous Anaphylaxis (PCA) screening test used to evaluate the present compounds is generally regarded as one of the best animal models for use in predicting the antiallergy activity of test compounds in man. Briefly, the method consists of passive sensitization of skin sites on the test animals with reaginic antibodies followed after 24 hours by administration of the test drug and antigen challenge. The allergic response is measured by use of Evans'blue dye and is evaluated by the spot diameter at the injection site. Details of the test are provided below.

Materials

Ovalbumin (5 times crystalline) Dinitrobenzene sulfonic acid, $Na^+$salt Bordetella pertussis vaccine - phase I 10–20 $\times$ 10$^9$ killed organisms/ml. Aluminum hydroxide gel - 10 mg./ml. Potassium carbonate Male Sprague-Dawley (S/D) Rats - 200 gms. Female Sprague-Dawley Rats - 100 gms. Tris Buffered Saline (TBS) - 0.02 M 2-amino-2-hydroxymethyl-1,3-propanediol (Tris), 0.15 M MaCL, pH 8.2

Antigen Preparation - DNP-d EA

A substituted ovalbumin antigen is used both as immunogen and challenging antigen. The antigen is prepared as follows: 500 mg. ovalbumin (EA) and 500 mg. $K_2CO_3$ are dissolved in 25 ml. distilled $H_2O$ and stirred at room temperature for 5 minutes. Five hundred (500)mg. dinitrobenzene sulfonic acid, $Na^+$salt, (previously recrystallized from hot absolute ethanol) is then added slowly with continued stirring. The reaction mixture is then immediately placed in the dark and allowed to proceed for 2 hours with constant stirring. After 2 hours the mixture is placed in suitable dialysis tubing and dialyzed against 5 changes (4 liters each) of distilled $H_2O$ at 5° C. After dialysis the product is lyophilized and stored at room temperature in a brown or amber container. The antigen obtained will appear as a light yellow, amorphous solid which is very soluble in water or saline. It is designated as DNP denatured ovalbumin (DNP-d EA).

Immunization Method for IgE Production

Adult, male Sprague-Dawley rats are used as a source of reagin-rich antisera for the PCA model. Immunization is by a combinatin of DNP-d EA on $Al(OH)_3$ gel and B. pertussis vaccine. Preparation of the DNP-d EA - gel immunogen is as follows: Dissolve the DNP-d EA in TBS so as to give a concentration of 10 mg./ml. Slowly add 1 ml. of this solution to 10 ml. $Al(OH)_3$ gel (10 mg. solids/ml.) with constant stirring at room temperature. Stir the mixture an additional 30 minutes to insure a uniform adsorption of antigen on gel.

The resulting preparation is then used in combination with phase I B. pertussis vaccine to immunize male S/D rats as follows: For each rat administer 0.1 ml. DNP-d EA - gel suspension intramuscularly in each hind leg (200 μg DNP-d EA and 2 mg. gel total dose). Follow these injections by the intraperitoneal administration of 1.0 ml. B. pertussis vaccine (10-20 × 10⁹ organisms). The use of light ether anesthesia during this procedure is recommended to insure proper intramuscular and intraperitoneal injections. 9 days following immunization (but no longer than 10) the animals are exsanguinated by cardiac puncture or abdominal aorta cannulation under ether or pentobarbital anesthesia. The collected whole blood is allowed to clot, the serum separated by centrifugation and the individual serum samples stored frozen until assayed for IgE content.

Selection of High Titered Serum Samples for Pooling

Individual serum samples should be screened for reaginic antibody concentration before being pooled with other sera, as not all rats respond to immunization procedures with reagin production. At 1:50 saline dilution of serum from each immunized rat is used for this purpose. Intradermal injections of 0.05 ml. of the diluted sera are made in the shaven backs of two small female recipient rats, 100–120 gms. Several serum samples can be tested simultaneously in recipient animals. After a 24 to 48 hour latent period antigen challenge is accomplished by intravenous administration to each rat of 1 mg. DNP-d EA in 0.5 ml. 0.5% Evans' blue dye in saline. Sera which show positive PCA reactions at the 1:50 dilution, as measured 20 to 30 minutes post-challenge are pooled, dispensed in small aliquots and stored at −70° C. or lower until used. Negative sera may be discarded.

The IgE titer of the antisera pool should then be determined. Serial two-fold dilutions (1:5 to 1:160) of unheated sera and sera heated at 56° C. for 1 hour are prepared in saline and 0.05 ml. of each dilution injected intradermally on the backs of female recipient rats. At least four animals should be used for both the heated and unheated serum titrations. After a 24-hour latent period each group is challenged with 1 mg. DNP-d EA in 0.5 ml. 0.5% Evans' blue dye. Reactions are read by reflecting the skin 20 to 30 minutes post-challenge. Intensity (blueing) and spot diameter should be measured and recorded. The pool titer is defined as the reciprocal of the greatest dilution of unheated serum which yields a measurable PCA response (>6 mm. dimeter) in at least half of the recipient animals. Antiserum pools having a titer of 50 or greater are acceptable for the PCA screen. These pools should be sterile-filtered and stored at −70° C. or lower until use. Lyophilization in small aliquots may be used as an alternate.

PCA Screening Method

1. Animals — Young female Sprague-Dawley rats, 90–110 gms. should be use. The rats should be conditioned (acclimatized) for at least five days prior to use, with food and water ad lib.

2. Passive Sensitization — The test animals are prepared for passive sensitization by carefully shaving areas on each side of the back with a fine toothed clipper. Using a 27 gauge five-eighths inch needle mounted on a 1 ml. tuberculin syringe make intradermal injections of saline dilutions of the antiserum pool. Four dilutions (two on either side) of antiserum are used. The exact dilutions used depend on the titer of the pool. For example, if the antiserum pool has a titer of 50, then dilutions of 1:10, 1:20, 1:30 and 1:40 are used; if the pool titers at 100, then the dilutions would be 1:20, 1:40, 1:60 and 1:80. The sequence of placement of each dilution should be either clockwise or counter-clockwise to facilitate ease in scoring. The latent period should be at least 24 but no more than 48 hours.

3. Drug Administration-Standard and Unknowns — Four animals are used for each test compound. Disodium cromoglycate (DSCG), solubilized in saline, is administered by intravenous (i.v.) route at the time of antigen challenge. The tetrazole test compounds are solubilized in aqueous sodium bicarbonate. The test compounds are administered i.v. or per os (p.o.) either 1–5 or 10 minutes, respectively, prior to antigen challenge.

4. Antigen Challenge and Reaction Evaluation - Elicitation of the PCA response is accomplished by intravenous administration of 1 mg. DNP-d EA in 0.5 ml. 0.5% Evans' blue dye in saline to each test rat. PCA reactions are maximal twenty to thirty minutes post-challenge. Reactions should be scored visually for color intensity and the average diameter of the spots measured at each antiserum dilution site. Both operations should be done by reflecting the skin. For comparative purposes the numbers in the control group (untreated) should be at least 5% and usually 10%, of the total animals tested on a particular day.

Observed drug inhibition is reported as percent reduction in effective antiserum titer in treated versus control groups.

Results

Test results for certain of the preferred compounds of the present invention by i.v. and p.o. routes of administration are shown below in Table I along with data for DSCG. The results are given in terms of the ID$_{50}$ value, i.e., the dose of compound that inhibits 50% of the response.

Table I

Rat PCA Screening Data for 2-Phenyl-5-(5-1H-tetrazolyl)pyrimidin-4(3H)-ones

Compound

| Example No. | R¹ | R² | ID$_{50}$ in mg./kg. i.v. | p.o. |
|---|---|---|---|---|
| 6 | OCH$_3$ | H | — | ~0.1 |
| 1 | OC$_2$H$_5$ | H | 0.02 | 0.09 |
| 2 | OCH$_2$CH$_2$CH$_3$ | H | — | 0.04 |
| 3 | OCH(CH$_3$)$_2$ | H | — | ~0.04 |
| 4 | OCH$_2$CH$_2$CH$_2$CH$_3$ | H | — | ~0.07 |
| 5 | OCH(CH$_3$)CH$_2$CH$_3$ | H | — | 0.05 |
| 7 | OCH$_2$CH(CH$_3$)$_2$ | H | — | ~0.1 |
| 8 | OCH$_2$—CH=CH$_2$ | H | — | 0.24 |
| 9 | OCH$_2$—◁ | H | — | 0.07 |
| 10 | OCH$_2$CH$_2$CH$_3$ | OCH$_3$ | — | 0.03 |
| 14 | OCH$_2$CH$_2$CH$_3$ | NO$_2$ | — | 5 |
| 15 | OCH$_2$CH$_2$CH$_3$ | NH$_2$ | — | ~0.1 |
| 16 | OCH$_2$CH$_2$CH$_3$ | N(CH$_3$)$_2$ | — | ~0.4 |
| DSCG | | | 0.3 | >>30 |

The following examples are provided solely for the purpose of illustrating preparation of the starting materials and compounds of the present invention and are not to be construed as limitations of the invention. All temperatures referred to below are in degrees Centigrade. "Skellysolve B" is a petroleum ether fraction of b.p. 60–68° C. consisting essentially of n-hexane (trade name of Skelly Oil Co.).

Preparation of Starting Materials

The substituted benzamidine (or benzamidine salt) starting materials may be prepared according to the procedures illustrated below.

Preparation 1: 2-Ethoxybenzamidine hydrochloride

To a cooled (ice-water) solution of triethyloxonium fluoroborate 8100 g., 0.53 mole) in 226 ml. of methylene chloride was added all at once a suspension of 2-ethoxybenzamide (87 g., 0.53 mole) in 915 ml. of methylene chloride. The resulting solution was stirred at room temperature for 36 hours. The solution was concentrated to one-third volume and diluted with about 600 ml. of diethyl ether, thereby precipitating the crude ethyl 2-ethoxybenzimidate fluoroborate (130 g., m.p. 116°–133°).

The above salt was suspended in 500 ml. of cold 10% ethanolic ammonia and the solution stirred at room temperature for 36 hours. The solution was reduced to dryness and the residue partitioned between ethyl acetate and 5N NaOH. The ethyl acetate layer was dried to give a viscous oil. About 200 ml. of acetonitrile was added to the oil whereupon a solid separated and was recovered to yield 36 g. of material, melting at 180°–183°. The solid was dissolved in about 60 ml. of methanol and acidified with hydrogen chloride. Addition of about 1 liter of dry ether precipitated the desired hydrochloride salt (31.2 g., m.p. 198°–199°).

Preparation 2: 2-Ethoxybenzamidine hydrochloride (alternate procedure)

Methyl fluorosulfonate (14.5 g., 0.127 mole) was added to a solution of 2-ethoxybenzamide (20.0 g., 0.121 mole) in methylene chloride (324 ml.). After three hours the solvent was removed under reduced pressure. The residue was triturated with diethyl ether and the mixture filtered. The collected crude ethyl 2-ethoxybenzimidate fluorosulfonate (28.5 g.), m.p. 83°–110°, was added to saturated ammoniacal ethanol (120 ml.). The mixture was stirred at room temperature for four days. The mixture was filtered and the filtrate concentrated. The residue was triturated with 2N sodium hydroxide and the resulting mixture extracted with ethyl acetate. The extract was dried over sodium sulfate and then concentrated. A solution of the residual oil in acetonitrile (50 ml.) was treated with hydrogen chloride. Addition of diethyl ether (700 ml) precipitated 2-ethoxybenzamidine hydrochloride (11.0 g., m.p. 193°–196°).

Preparation 3: 2-Ethoxybenzamidine

To a solution of 2-ethoxybenzamide (13.0 g., 0.0785 mole) in 34 ml. of dry methylene chloride was added all at once a suspension of triethyloxonium fluoroborate (15.0 g., 0.0785 mole) in 137 ml. of methylene chloride. The solution which formed immediately upon addition of the fluoroborate was stirred for 19 hours at room temperature. The solution was concentrated to about one-third volume and diluted with about 100 ml of diethyl ether to precipitate the ethyl 2-ethoxybenzimidate fluoroborate which, when collected and dried, weighed 19.2 g., m.p. 113°–116°.

The above imidate fluoroborate was then added to 100 ml. of ethanol containing 1.4 g. of $NH_3$. The resulting solution was stirred for 78 hours at room temperature while keeping the flask tightly stoppered. The solvent was removed under reduced pressure to give a colorless solid which was dissolved in a small volume of water and basified with 6N NaOH. After extraction with ethyl acetate, the solvent extract was dried to yield 7.4 g. of title product, m.p. 78°–84°.

Replacement of the 2-ethoxybenzamide used above by an equimolar amount of 2-isopropoxybenzamide of 2-n-propoxybenzamide gives 2-isopropoxybenzamidine and 2-n-propoxybenzamidine, respectively.

Preparation 4: 2-Ethoxybenzamidine fluorosulfonate (Method A)

To a suspension of 2-ethoxybenzamide (500 g., 3.03 moles) in methylene chloride (12.5 l.) was added methyl fluorosulfonate (256 ml., 3.17 moles). The resulting solution was stirred at room temperature for 3 hours. The solvent was removed under vacuum. The residue was triturated with diethyl ether and the mixture filtered. The collected solid was washed with ether and then added to a cold (ice-water) solution of ammonia (500 g.) in ethanol (3 l.). The mixture was stirred in the cold for 0.5 hour and then at room temperature for 16 hours. The solution was concentrated and the residue crystallized from 1,2-dichloroethane to give 2-ethoxybenzamidine fluorosulfonate (517 g., 65%), m.p. 98°–99°.

Anal. Calcd. for $C_9H_{12}H_2O \cdot HFSO_3$: C, 40.90; H, 4.96; N, 10.60. Found: C, 40.95; H, 4.83; N, 10.73.

Preparation 5: 2-Ethoxybenzamidine fluorosulfonate (Method B)

To a suspension of 2-ethoxybenzamide (1 kg., 6.05 moles9 in methylene chloride (12.5 l.) was added methyl fluorosulfonate (538 ml., 6.66 moles). The mixture was stirred at room temperature for 18.5 hours. Ammonia gas was then bubbled into this mixture for 8 hours while the temperature of the mixture was maintained below 26°. The mixture was stirred for an additional 16 hours at room temperature. The solvent was removed under vacuum to leave crude 2-ethoxybenzamidine fluorosulfonate (1.7 kg.).

Preparation 6: 2-Ethoxybenzamidine methyl sulfate

A solution of 2-ethoxybenzamide (16.5 g., 0.1 mole) and dimethyl sulfate (19.0 ml., 0.2 mole) in 1,2-dichloroethane (60 ml.) was heated under reflux for 17 hours with stirring. The solvent was removed under reduced pressure. The residual oil was stirred for 0.5 hour with diethyl ether (200 ml.). The methyl 2-ethoxybenzimidate methyl sulfate was collected by filtration, dried, and then added to stirred, saturated ethanolic ammonia (150 ml.). The solution was allowed to stand at room temperature for 18 hours. The solution was filtered and the filtrate concentrated. The residue was triturated with diethyl ether after which the 2-ethoxybenzamidine methyl sulfate (19.9 g., 72% based on 2-ethoxybenzamide) was collected by filtration.

Preparation 7: 2-n-Propoxybenzamidine hydrochloride

A. Ethyl 2-n-Propoxybenzimidate fluoroborate - A solution of triethyloxonium fluoroborate (33.0 g., 0.175 mole) in methylene chloride (75 ml.) was added during 10 minutes to a stirred solution of 2-n-propoxybenzamide (31.3 g., 0.175 mole) in methylene chloride (150 ml.). The solution was stirred for an additional 18 hours at room temperature. The solution was concentrated to about one-fifth volume and was diluted with diethyl ether to precipitate the ethyl 2-propoxybenzimidate fluoroborate (44.0 g., 85% yield), m.p. 108°–112°.

B. 2-Propoxybenzamidine hydrochloride -

Ethanol (100 ml.) containing 6.5 g. of ammonia was added during five minutes to a stirred suspension of ethyl 2-n-propoxybenzimidate fluoroborate (44.0 g.) in ethanol (25 ml.). The resulting solution was stirred at 25° for 20 hours. The solution was reduced to dryness and the residue partitioned between diethyl ether and 5N sodium hydroxide. The ether layer was washed with brine, dried over sodium sulfate, and concentrated. A solution of the residue in ether (500 ml.) and ethanol (50 ml.) was treated with hydrogen chloride to precipitate 2-n-propoxybenzamidine hydrochloride (28.8 g., 76.6% yield), m.p. 184°–186.5°.

Preparation 8: 2-n-Propoxybenzamidine methyl sulfate

To a warm, stirred solution of 2-n-propoxybenzamide (896 g., 5.0 moles) in 1,2-dichloroethane (5 l) was added dimethyl sulfate (950 ml., 10.0 moles) over a period of about 0.5 hour. The mixture was stirred and heated under reflux for 17 hours. The solvent was removed. The residual oily solid was collected by filtration, washed with ethyl acetate and dried to give methyl 2-n-propoxybenzimidate methyl sulfate (403 g.), m.p. 79°–82°. The combined filtrate and washings were stored at 0° for 18 hours and gave a second crop (503 g.) of benzimidate, m.p. 81°–83°. A slurry of the methyl 2-n-propoxybenzimidate methyl sulfate (906 g.) in ethanol (1 l) was added to ethanol (4 l) which had previously been saturated with gaseous ammonia. The mixture was stored at room temperature for 17 hours. The mixture was filtered. The filtrate was evaporated to dryness to give 2-n-propoxybenzamidine methyl sulfate (872 g., 60%), m.p. 86°–88°.

Preparation 9: 2-Isopropoxybenzamidine hydrochloride

A solution of triethyloxonium fluoroborate (38.4 g., 0.202 mole) in methylene chloride (75 ml.) was added during 15 minutes to a stirred solution of 2-isopropoxybenzamide (36.2 g., 0.202 mole) in methylene chloride (100 ml.). The mixture was stirred for 18 hours at room temperature. The solution was concentrated to about one-fifth volume and was diluted with diethyl ether to precipitate colorless crystals (60 g., m.p. 90°–110°) of crude ethyl 2-isopropoxybenzimidate fluoroborate. Recrystallization of this material from methylene chloride-diethyl ether gave 55 g. of colorless material, m.p. 114°–120°.

To a stirred suspension of the above fluoroborate (55 g.) in ethanol (50 ml.) was added 150 ml. of 8% ethanolic NH$_3$. The mixture was stirred for 64 hours at 25°. The solution was reduced to dryness and the residue made basic with 100 ml. of 5 N NaOH. The basic mixture was extracted with ether and the ethereal extract dried. A solution of the residue in ether (500 mml.) and ethanol (50 ml.) was treated with hydrogen chloride to precipitate 24.1 g. of colorless 2-isopropoxybenzamidine hydrochloride, m.p. 162°–164°.

Preparation 10: 2-n-Butoxybenzamidine hydrochloride

A solution of triethyloxonium fluoroborate (32.4 g., 0.171 mole) in methylene chloride (75 ml.) was added to a stirred solution of 2-n-butoxybenzamide [J. Pharm. Pharmacol., 4, 872 (1952) ](33.0 g., 0.171 mole) in methylene chloride 8200 ml.) at 25°. The mixture was stirred at 25° for 20 hours. The solution was concentrated to about one fifth of the original volume and then diluted with diethyl ether. The precipitated solid was recrystallized from methylene chloride-diethyl ether to give ethyl 2-n-butoxybenzimidate fluoroborate (28.7 g.), m.p. 82°–88°. To a stirred, cooled (ice-water) suspension of the fluoroborate (28.7 g.) in ethanol (75 ml.) was added 8% ethanolic ammonia (150 ml.). The mixture was stirred at 25° for 20 hours. The ethanol was removed and the residue partitioned between ether and 5N sodium hydroxide (100 ml.). The ether layer was washed with brine, dried over sodium sulfate, and then concentrated. A solution of the residual oil in ether was treated with hydrogen chloride to precipitate the title compound (16.8 g.), m.p. 150°–155°.

Preparation 11: (±)-2-sec-Butoxybenzamidine hydrochloride

In a manner similar to that described for the preparation of 2-n-butoxybenzamidine hydrochloride in Preparation 10 above (±)-2-sec-butoxybenzamidine hydrochloride, m.p. 142°–144°, was prepared from (±)-2-sec-butoxybenzamide which itself is disclosed in J. Pharm. Pharmacol., 9 855(1957).

Preparation 12: 2-Isobutoxybenzamidine

A cold (ice-water) solution of 2-isobutoxybenzamide[1] (70.1 g., 0.363 mole) in methylene chloride (800 ml.) was added to a cold solution of triethyloxonium fluoroborate (69.0 g., 0.363 mole) in methylene chloride (175 ml.). The resulting solution was stirred at room temperature for 16 hours. Approximately two thirds of the solvent was removed and the residue diluted with diethyl ether (500 ml.). The mixture was filtered. The collected ethyl 2-isobutoxybenzimidate fluoroborate[1] (76.5 g.), m.p. 110°–112°, was added to ethanol (350 ml.) saturated with gaseous ammonia. After 67 hours at room temperature the solution was evaporated to dryness. The residue was treated with 5N sodium hydroxide (160 ml.). The mixture was extracted with methylene chloride (3 × 200 ml.) and the combined extracts were washed with water, dried (sodium sulfate) and concentrated. The residue was recrystallized from cyclohexane to give 2-isobutoxybenzamidine[1] (42.9 g., 61.5% overall), m.p. 49-51°.

Anal. Calcd. for $C_{11}H_{16}N_2O$: C, 68.72; H, 8.39; N, 14.57. Found: C, 68.60; H, 8.42; N, 14.28.

Reference
1. B. J. Broughton, B. J. Large, S. M. Marshall, D. L. Pain and K. R. H. Wooldridge, U.S. Pat. No. 3,819,631 (1974).

Preparation 13: 2-Isobutoxybenzamidine fluorosulfonate

Methyl fluorosulfonate (5.65 g., 0.0495 mole) was added to a stirred solution of 2-isobutoxybenzamide[1] (8.6 g., 0.0445 mole) in methylene chloride (100 ml.) under nitrogen. The solution was stirred at room temperature for 18 hours. Ammonia gas was then bubbled through the solution for 3 hours with stirring. The solution was concentrated and the residue recrystallized from 1,2-dichloroethane to give the title compound (1.1 g., 8.5% yield).

Reference
1. B. J. Broughton, B. J. Large, S. M. Marshall, D. L. Pain and K. R. H. Wooldridge, U.S. Pat. No. 3,819,631 (1974).

Preparation 14: 2-Ethoxy-5-methoxybenzamidine hydrochloride A. 2-Ethoxy-5-methoxybenzamide 5-Methoxysalicylamide (41.8 g., 0.250 mole) was dissolved in a solution of sodium (6.37 g., 0.277 g-atom) in ethanol (250 ml.). To the resulting cooled (ice-water) solution was added iodoethane (38.9 g., 0.250 mole) over a period of 20 minutes. The reaction mixture was allowed to warm to room temperature over 0.75 hour and then was heated under reflux for 19 hours. The mixture was concentrated and the residue triturated with water. The mixture was filtered and the collected solid recrystallized from acetonitrile to give 2-ethoxy-5-methoxybenzamide (34.5 g., 70.7%), m.p. 128°–130°.

Anal. Calcd. for $C_{10}H_{13}NO_3$: C, 61.52; H, 6.71; N, 7.18. Found: C, 61.45; H, 6.51; N, 6.93.

B. 2-Ethoxy-5-methoxybenzamidine hydrochloride

Methyl fluorosulfonate (28.4 g., 0.248 mole) was added to a cooled (ice-water) solution of 2-ethoxy-5-methoxybenzamide (33.5 g., 0.172 mole) in methylene chloride (450 ml.) over a period of 20 minutes. The mixture was stirred at room temperature for 4 hours. Two thirds of the solvent was removed and the residue diluted with diethyl ether. The precipitated crude methyl 2-ethoxy-5-methoxybenzimidate fluorosulfonate (50.0 g.), m.p. 144°–152° was dissolved in cold ethanol (300 ml.) which had been saturated with ammonia. The mixture was stirred with cooling (ice-water) for 2 hours followed by 17 hours at room temperature. The ethanol was removed under reduced pressure to give a semi-solid which was treated with 5N sodium hydroxide (200 ml.). The mixture was extracted with ethyl acetate. The extract was dried (sodium sulfate) and concentrated. A solution of the residue in acetonitrile-acetone (2:5) was treated with hydrogen chloride gas to precipitate 2-ethoxy-5-methoxybenzamidine hydrochloride (10.5 g., 26.5%), m.p. 166°–167°.

Preparation 15: 5-Carbomethoxy-2-ethoxybenzamidine

A: 5-Carbomethoxy-2-ethoxybenzamide

5-Carbomethoxy-2-ethoxybenzamide (m.p. 159°–161°) was prepared from 5-carbomethoxysalicylamie, iodoethane, and sodium methoxide in methanol in a manner analogous to that described for the preparation of 2-ethoxy-5-methoxybenzamide in Preparation 14A.

B: 5-Carbomethoxy-2-ethoxybenzamidine

5-Carbomethoxy-2-ethoxybenzamidine, m.p. 133°–135°, was prepared from 5-carbomethoxy-2-ethoxybenzamide in a manner similar to that described for the preparation of 2-isobutoxybenzamidine in Preparation 12.

Preparation 16: 5-Chloro-2-ethoxybenzamidine hydrichloride

A: 5-Chloro-2-ethoxybenzamide

A mixture of 5-chlorosalicylamide (16.0 g., 0.093 mole), iodoethane (31.8 g., 0.204 mole), and potassium carbonate (13.1 g., 0.095 mole) in ethanol (225 ml.) was heated under reflux for 20 hours. The hot mixture was filtered. The filtrate was reduced to dryness. The residue was triturated with water. The mixture was filtered and the collected solid recrystallized from acetonitrile to give 5-chloro-2-ethoxybenzamide (6.8 g., 36.6%) m.p. 136°–139°.

Anal. Calcd. for $C_9H_{10}ClNO_2$: C, 54.15; H, 5.05; Cl, 17.76; N, 7.02. Found: C, 54.25; H, 4.85; Cl, 17.42; N, 6.89.

B: 5-Chloro-2-ethoxybenzamidine hydrochloride

If the procedure of Preparation 10 is repeated with the 2-n-butoxybenzamide used therein replaced by an equimolar amount of 5-chloro-2-ethoxybenzamide, there is produced the title product, m.p. 227° with decomposition.

Anal. Calcd. for $C_9H_{11}ClN_2O \cdot HCl$: C, 45.97; H, 5.15; N, 11.91. Found: C, 46.23; H, 5.20; N, 11.87.

Preparation 17: 2,5-Dimethoxybenzamidine hydrochloride

If the procedure of Preparation 10 is repeated with the 2-n-butoxybenzamide used therein replaced by an equimolar amount of 2,5-dimethoxybenzamide, there is produced the title product, m.p. 170°–172°.

Preparation 18: 2-cyclopropylmethoxybenzamidine hydrochloride

A: 2-cyclopropylmethoxybenzamide

A stirred mixture of salicylamide (10.02 g., 0.074 mole), potassium carbonate (10.24 g., 0.074 mole) and bromomethylcyclopropane (10.0 g., 0.074 mole) in ethanol (15 ml.) was heated under reflux for 19 hours. The mixture was concentrated and the residue treated with water. The mixture was filtered and the collected solid recrystallized from benzene-Skellysolve B to give 2-cyclopropylmethoxybenzamide (10.0 g., 71.6%), m.p. 102°–105°.

B: 2-Cyclopropylmethoxybenzamidine hydrocloride

A solution of triethyloxonium fluoroborate (99.1 g., 0.522 mole) in methylene chloride (225 ml.) was added to a stirred solution of 2-cyclopropylmethoxybenzamide (99.2 g., 0.518 mole) in methylene chloride (450 ml.). The mixture was stirred at 22° for 18 hours. The solution was concentrated to about one-fifth volume and then diluted with diethyl ether. The precipitated solid was recrystallized from methylene chloride - diethyl ether to give ethyl 2-cyclopropylmethoxybenzimidate fluoroborate (104.7 g., 65.7%), m.p. 120°–121°. To a stirred, cooled (ice-water) mixture of the fluoroborate (104.7 g.) in ethanol (100 ml.) was added 400 ml. of 6% ethanolic ammonia. The mixture was stirred for 18 hours at 20°. The mixture was concentrated and the residue partitioned between diethyl ether and 3N sodium hydroxide. The ether layer was washed with brine and dried over sodium sulfate. The dried solution was treated with hydrogen chloride. The precipitate was recrystallized from methylene chloride-diethyl ether to give 2-cyclopropylmethoxybenzamidine hydrochloride (71.5 g., 92.5% from fluoroborate), m.p. 166°–171°.

Preparation 19: 5-Methoxy-2-n-propoxybenzamidine hydrochloride

A: 5-Methoxy-2-n-propoxybenzamide

5-Methoxysalicylamide (56.0 g., 0.335 mole) was added to a cooled, stirred solution of sodium (8.55 g., 0.372 g-atom) in ethanol (335 ml.). To the resulting suspension was added 1-bromopropane (41.3 g., 0.335 mole) dropwise over 20 minutes. The mixture was stirred at room temperature for one hour, then was heated under reflux for 19 hours. The solvent was removed under reduced pressure. The residue was treated with cold water (500 ml.). The solid was collected by filtration and recrystallized from acetonitrile to give 5-methoxy-2-n-propoxybenzamide (29.0 g., 41.4%), m.p. 83°–87°.

Anal. Calcd. for $C_{11}H_{15}NO_3$: C, 63,14; H, 7.23; N, 6.69. Found: C, 63.28; H, 7.43; N, 6.47.

B: 5-Methoxy-2-n-propoxybenzamidine hydrochloride

To a solution of 5-methoxy-2-n-propoxybenzamide (29.0 g., 0.139 mole) in methylene chloride (200 ml.) at 5° was added methyl fluorosulfonate (15.8 g., 0.139 mole). The solution was stirred at room temperature for 5 hours. Most of the solvent was removed and the residual solution diluted with diethyl ether (500 ml.). The precipitated methyl 5-methoxy2-n-propoxybenzimidate fluorosulfonate (35.4 g., m.p. 117°–126°) was collected and added to cold, saturated ethanolic ammonia (220 ml.). The mixture was stirred at room temperature for 19 hours. The solution was concentrated and the residual oil dissolved in a mixture of acetonitrile and ether. The resulting solution was treated with hydrogen chloride to precipitate 5-methoxy-2-n-propoxybenzamidine hydrochloride (31.5 g.) as an oil, which was separated by decantation of the solvents.

Preparation 20-1: 2-Methoxybenzamidine hydrochloride

In a manner similar to that described for the preparation of 2-n-propoxybenzamidine hydrochloride in Preparation 7, 2-methoxybenzamindine hydrochloride, m.p. 150°–152° was prepared from 2-methoxybenzamide.

Preparation 20-2: 2-Ethylthiobenzamidine hydrochloride

A. 2-Ethylthiobenzamidoxime

A solution of 2-ethylthiobenzonitrile (29.0 g., 0.178 mole) [disclosed by K. Brand and H. Stein in J. Prakt. Chem., 108, 19 (1924)] in ethanol (284 ml.) was added over a 30 minute period to a solution of hydroxylamine hydrochloride (4.47 g., 0.64 mole) and sodium carbonate (31.2 g., 0.29 mole) in water (474 ml.). The mixture was heated under reflux for 1.75 hours. The cooled mixture was reduced to one third volume. The residue was partitioned between diethyl ether and 1N hydrochloric acid. The ether and aqueous layers were separated. The ether layer was extracted twice with fresh 1N HCl. The combined aqueous layer were adjusted to pH 5.5 with sodium bicarbonate. The mixture was extracted with ether (3 × 200 ml.). The combined ether extracts were dried (sodium sulfate) and concentrated to give 2-ethylthiobenzamidoxime (12.5 g., 36%), m.p. 72-78°. Recrystallization from 2-propanol-ether gave analytical material, m.p. 79°–83°.

Anal. Calcd. $C_9H_{12}N_2OS$: C, 55.09; H, 6.17; N, 14.28. Found: C, 54.92; H, 6.27; N, 14.08.

B. 2-Ethylthiobenzamidine hydrochloride

Raney nickel was added to a solution of 2-ethylthiobenzamidoxime (6.0 g., 30.6 mmoles) in ethanol (200 ml.) and the mixture shaken for 3 hours in an atmosphere of hydrogen at an initial pressure of 3.5 kg./cm². The mixture was filtered and the filtrate concentrated. The residual oil was dissolved in a mixture of ethanol (30 ml.) and diethyl ether (400 ml.). The solution was treated with hydrogen chloride. The precipitated 2-ethylthiobenzamidine hydrochloride, m.p. 290°–291° (2.4 g., 36.2%), was recrystallized from 2-propanol-ether to give analytical material, m.p. 296°–297°.

The 1,6-dihydro-6-oxo-2-phenyl-pyrimidine-5-carboxylate esters (general formula V) may be prepared as follows:

Preparation 21: Ethyl 1,6-dihydro-6-oxo-2-(2-ethoxyphenyl)-pyrimidine-5-carboxylate (illustrates use of benzamidine free base)

To a cooled solution of sodium (1.04 g., 0.045 g-atom) in 35 ml. of ethanol was added all at once 2-ethoxybenzamidine (7.4 g., 45 mmole). There was then added to this suspension over a 5 minute period a solution of diethyl ethoxymethylenemalonate (9.7 g., 45 mmole) in 20 ml. of ethanol whereupon a pale yellow precipitate soon formed. An additional 25 ml. of ethanol was added to the reaction mixture which was then heated under reflux for 2 1/4 hours. The cooled solution was poured into about 500 ml. of ice-water and acidified with 6N HCl to produce a pale yellow solid. The solid was dried to give 10.2 g., 144°–149°, of title product. recrystallization from acetonitrile gave 9.8 g., m.p. 147°–150°, of purified product.

Anal. Calcd. for $C_{15}H_{16}N_2O_4$: C, 62.49; H, 5.60; N, 9.72 Found: C, 62.23; H, 5.57; N, 9.63

Preparation 22: Ethyl 1,6-dihydro-6-oxo-2-(2-ethoxyphenyl)-pyrimidine-5-carboxylate (illustrates use of benzamidine hydrochloride salt)

To a cooled solution of sodium (8.2 g., 0.356 g-atom) in 300 ml. ethanol was added all at onece 2-ethoxybenzamidine hydrochloride (35.7 g., 0.178 mole). A solution of diethyl ethoxymethylenemalonate (38.4g., 0.178 mole) in 80 ml. of ethanol was added to the suspension and the mixture was heated under reflux for 2¼ hours. The cooled solution was added to about 2800 ml. of ice-water and the mixture was acidified to pH 5 with glacial acetic acid. The precipitated title product was dried to give 47 g. of an off-white solid, m.p. 147°–150°.

Preparation 23: Ethyl 1,6-dihydro-6-oxo-2-(2-ethoxyphenyl)-pyrimidine-5-carboxylate (illustrates use of benzamidine fluorosulfonate)

To a solution of sodium ethoxide at 18° prepared from sodium (41 g., 1.78 g-atoms) in ethanol (1 l.), was added a solution of 2-ethoxybenzamidine fluorosulfonate (206.5 g., 0.78 mole) in ethanol (500 ml.). The resulting solution was cooled to 13° and then treated with a solution of diethyl ethoxymethylenemalonate (180 ml., 0.89 mole) in ethanol (400 ml.). The mixture was heated under reflux for 2.25 hours. The mixture was cooled to 10° and then poured into cold water (5 l.) with good stirring. Ice was added as necessary to keep the temperature of the mixture below 20°. the mixture was acidified to pH 5 with glacial acetic acid. The solid material was collected by filtration, washed with water, and dried to give the title compound (218.7 g., 97%). Recrystallization from acetonitrile gave product with m.p. 144°–147°.

Preparation 24: Ethyl 1,6-dihydro-6-oxo-2-(2-ethoxyphenyl)-pyrimidine-5-carboxylate (illustrates most preferred procedure using benzamidine methyl sulfate)

2-Ethoxybenzamidine methyl sulfate (19.9 g., 0.072 mole) followed by diethyl ethoxymethylenemalonate (17.0 g., 0.079 mole) were added to a stirred solution of sodium (3.3 g., 0.144 g-atom) in ethanol (150 ml.). The mixture was heated under reflux for 2.25 hours. The cooled mixture was poured into ice-water (250 ml.) which was then acidified with glacial acetic acid. The title compound was collected by filtration, washed with water and dried. The product (16.0 g., 77%), had m.p. 138°–140°.

Preparation 25: Ethyl 1,6-dihydro-6-oxo-2-(2-n-propoxyphenyl)pyrimidine-5-carboxylate (benzamidine hydrochloride)

2-Propoxybenzamidine hydrochloride (12.0 g., 0.0558 mole) was added to a stirred, cooled (ice-water) solution of sodium (2.57 g., 0.112 g-atom) in ethanol (50 ml.). To this cooled, stirred solution was added a solution of diethyl ethoxymethylenemalonate (12.1 g., 0.0558 mole) in ethanol (50 ml.) during 10 minutes. The mixture was heated under reflux for 2.5 hours. The cooled solution was poured onto ice and acidified with 6N hydrochloric acid. The precipitated ethyl 1,6-dihydro-6-oxo-2-(2-n-propoxyphenyl)pyrimidine-5-carboxylate (16.2 g., 96% yield) had m.p. 111°–113°. Two recrystallizations from cyclohexane gave title product with m.p. 112°–113°.

Anal. Calcd. for $C_{16}H_{18}N_2O_4$: C, 63.56; H, 6.00; N, 9.27. Found: C, 63.59; H, 6.15; N, 9.47.

Preparation 26: Ethyl 1,6-Dihydro-6-oxo-2-(2-n-propoxyphenyl)-pyrimidine-5-carboxylate (benzamidine methyl sulfate with sodium ethoxide)

To a warm solution of sodium (181.7 g., 7.9 g-atoms) in ethanol (5 l) was added with stirring a slurry of 2-n-propoxybenzamidine methyl sulfate (1146.7 g., 3.95 moles) in ethanol 1.6 l). After 2-3 minutes diethyl ethoxymethylenemalonate 854 g., 3.95 moles) was added and the mixture stirred and heated under reflux for 2.25 hours. The mixture was cooled and then added to cold water (13 l). The mixture was acidified to pH 5-6 with glacial acetic acid. The solid was collected by filtration, washed with water, and dried to give the title compound (937.8 g.), m.p. 102°–104°. An additional crop of product (101.6 g., m.p. 105°–107°, was obtained from the filtrate and washings. Total yield of product, 1039.4 g. (87%).

Preparation 27: Ethyl 1,6-dihydro-6-oxo-2-(2-n-propoxyphenyl)pyrimidine-5-carboxylate (benzamidine methyl sulfate with $K_2CO_3$)

A mixture of 2;1-n-propoxybenzamidine methyl sulfate (7.4 g., 0.0255 mole), potassium carbonate (3.53 g., 0.025 mole), and diethyl ethoxymethylenemalonate (5.99 g., 0.0277 mole) in ethanol (80 ml.) was heated under reflux with stirring for 17 hours. The cooled mixture was added to ice-water (160 ml.) which was then acidified with glacial acetic acid. The precipitate was collected by filtration, washed with water, and dried to give the title compound (6.55 g., 89%), m.p. 106°–107°.

Preparation 28: Ethyl 1,6-dihydro-6-oxo-2-(2-isopropoxyphenyl)pyrimidine-5-carboxylate (benzamidine hydrochloride)

2-Isopropoxybenzamidine hydrochloride (10.0 g., 0.0465 mole) was added to a stirred, cooled (ice-water) solution of sodium (2.14 g., 0.093 g-atom) in ethanol (100 ml.). To this cooled, stirred solution was added dropwise a solution of diethyl ethoxymethylenemalonate (10.1 g., 0.0465 mole) in ethanol (30 ml.) over a 10 minute period. The mixture was refluxed for 2 hours and stored at 22° for 18 hours. The mixture was then poured onto ice-water containing acetic acid (10 ml.) and concentrated HCl (10 ml.) to precipitate the desired product. The precipitate was washed and dried to give 15.5 g. of the title product, m.p. 123°–124°. Recrystallizations from ethyl acetate and then cyclohexane gave colorless crystals of the ester, m.p. 128°–130°.

Anal. Calcd. for $C_{16}H_{18}N_2O_4$: C, 63.56; H, 6.00; N, 9.27. Found: C, 63.60; H, 5.93; N, 9.29.

Preparation 29: Ethyl 1,6-dihydro-6-oxo-2-(2-allyloxyphenyl)pyrimidine-5-carboxylate (benzamidine hydrochloride)

2-Allyloxybenzamidine hydrochloride[1] (19.07 g., 0.0896 mole) was added to a cooled (ice-water), stirred solution of sodium ethoxide (12.25 g., 0.18 mole) in ethanol (100 ml.). To this cooled, stirred mixture was added a solution of diethyl ethoxymethylenemalonate (19.4 g., 0.0896 mole) in ethanol (15 ml.). The mixture was heated under reflux for 2.5 hours and then allowed to stand at room temperature for 18 hours. The mixture was poured into ice-water containing acetic acid. The solid was collected and recrystallized from cyclohexane to give the title compound (24.0 g., 89%), m.p. 118°–120°. Recrystallization from cyclohexane gave product with m.p. 118.5°–120.5°.

Anal. Calcd. for $C_{16}H_{16}N_2O_4$: C, 63.99; H, 5.37; N, 9.33. Found: C, 63.93; H, 5.42; N, 9.36.

1. U.S. Pat. No. 3,819,631.

Preparation 30: Ethyl 1,6-dihydro-6-oxo-2-(2-n-butoxyphenyl)pyrimidine-5-carboxylate (benzamidine hydrochloride)

The procedure of Preparation 29 was repeated except that the 2-allyloxybenzamidine hydrochloride used therein was replaced with an equimolar amount of 2-n-butoxybenzamidine hydrochloride. There was produced the title product, m.p. 123°–125°.

Anal. Calcd. for $C_{17}H_{20}N_2O_4$: C, 64.54; H, 6.37; N, 8.86. Found: C, 64.41; H, 6.29; N, 9.07.

Preparation 31: Ethyl(±)-1,6-dihydro-6-oxo-2-(2-sec-butoxyphenyl)-pyrimidine-5-carboxylate (benzamidine hydrochloride)

In a manner similar to that described for the preparation of ethyl 1,6-dihydro-6-oxo-2-(2-n-butoxyphenyl)-pyrimidine-5-carboxylate in Preparation 30, ethyl (±)-1,6-dihydro-6-oxo-2-(2-sec-butoxyphenyl)pyrimidine-5-carboxylate, m.p. 134°–136°, was prepared from (±)-2-sec-butoxybenzamidine hydrochloride.

Anal. Calcd. for $C_{17}H_{20}N_2O_4$: C, 64.54; H, 6.37; N, 8.86. Found: C, 64.31; H, 6.12; N, 8.82.

Preparation 32: Ethyl 1,6-dihydro-6-oxo-2-(2-isobutoxyphenyl)pyrimidine-5-carboxylate (benzamidine free base)

To a stirred solution of sodium (3.15 g., 0.137 g-atom) in ethanol (250 ml.) was added 2-isobutoxybenzamidine (26.3 g., 0.137 mole) followed by diethyl ethoxymethylenemalonate (29.6 g., 0.137 mole). The mixture was heated under reflux for 3 hours. The cooled mixture was added to icewater (300 ml.) which was then acidified to pH 5 with glacial acetic acid. The crystalline product (36.4 g., 85%) m.p. 89°-91°, which formed on cooling was collected and a portion recrystallized from 50% aqueous ethanol to give the title compound, m.p. 92°-93°.

Anal. Calcd. for $C_{17}H_{20}N_2O_4$: C, 64.54; H, 6.37; N, 8.86. Found: C, 64.66; H, 6.64; N, 8.69.

Preparation 33: Ethyl 1,6-dihydro-6-oxo-2-(2-isobutyoxyphenyl)-pyrimidine-5-carboxylate (benzamidine fluorosulfonate)

To a solution of sodium (161 mg., 7 mg-atoms) in ethanol (10 ml.) was added 2-isobutoxybenzamidine fluorosulfonate (1.02 g., 3.5 mmole). The mixture was warmed to give a clear solution to which was added a solution of diethyl ethoxymethylenemalonate (756 mg., 3.5 mmole) in ethanol (2 ml.). The solution was heated under reflux for 3 hours. The cooled mixture was added to ice-water (50 ml.) and was acidified to pH 5 with glacial acetic acid. After brief stirring, the solid was collected by filtration, washed with water, and dried to give the title compound (0.94 g., 86%), m.p. 90-91°.

Preparation 34: Ethyl 1,6-dihydro-6-oxo-2-(2-isobutoxyphenyl)pyrimidine-5-carboxylate (use of $K_2CO_3$ in place of alkali metal alkoxide Diethyl ethoxymethylenemalonate (6.42 g., 0.03 mole) was added to a stirred mixture of 2-isobutoxybenzamidine (5.76 g., 0.03 mole) and potassium carbonate (4.14 g., 0.03 mole) in ethanol (70 ml.). The mixture was heated under reflux for 4 hours. The cooled mixture was added to water (100 ml.) which was then acidified to pH 8 with 6N hydrochloric acid and then to pH 5 with glacial acetic acid. The title compound was collected by filtration, washed with water, and dried. The product 6.76 g., 71%) had m.p. 88°-90°.

Preparation 35: Ethyl 1,6-dihydro-6-oxo-2-(2-isobutoxyphenyl)pyrimidine-5-carboxylate (coupling reaction without use of base condensing agent)

The experiment described above in Preparation 34 was repeated, but this time without the potassium carbonate. The title product was obtained in 69% yield, m.p. 89°-91°.

Preparation 36:

The following ethyl 1,6-dihydro-6-oxo-2-phenyl-pyrimidine-5-carboxylates were prepared from the corresponding benzamidine hydrochlorides according to the general method of Preparation 29.

A. Ethyl 1,6-dihydro-6-oxo-2-(2,5-dimethyoxyphenyl)pyrimidine-5-carboxylate, m.p. 149°-150°.

Anal. Calcd. for $C_{15}H_{16}N_2O_5$: C, 59.20; H, 5.30; N, 9.21. Found: C, 59.07; H, 5.27; N, 9.23.

B. Ethyl 1,6-dihydro-6-oxo-2-(5-chloro-2-ethoxyphenyl)pyrimidine-5-carboxylate, m.p. 209°-212°.

Anal. Calcd. for $C_{15}H_{15}ClN_2O_4$: C, 55.82; H, 4.68; Cl, 10.99; N, 8.68. Found: C, 55.66; H, 4.67; Cl, 10.87; N, 8.78.

C. Ethyl 1,6-dihydro-6-oxo-2-(2-ethoxy-5-methoxyphenyl-pyrimidine-5-carboxylate, m.p. 149°-152°.

Anal. Calcd. for $C_{16}H_{18}N_2O_5$: C, 60.37; H, 5.70; N, 8.80 Found: C, 60.31; H, 5.68; N, 9.09.

D. Ethyl 1,6-dihydro-6-oxo-2-(2-methoxyphenyl)pyrimidine-5-carboxylate, m.p. 148°-150°.

Anal. Calcd. for $C_{14}H_{14}N_2O_4$: C, 61.31; H, 5.14; N, 10.21. Found: C, 61.38; H, 5.05; N, 10.23.

E. Ethyl 1,6-dihydro-6-oxo-2-(2-chlorophenyl)pyrimidine-5-carboxylate, m.p. 139°-141°.

Anal. Calcd. for $C_{13}H_{11}ClN_2O_3$: C, 56.02; H, 3.98; Cl, 12.72; N, 10.05. Found: C, 55.90; H, 3.68; Cl, 12.34: N, 10.16

F. Ethyl 1,6-dihydro-6-oxo-2-(3-methoxyphenyl)pyrimidine-5-carboxylate, m.p. 169°-170°.

Anal. Calcd. for $C_{14}H_{14}N_2O_4$: C, 61.31; H, 5.14: N, 10.21. Found: C, 60.96; H, 5.13; N, 10.16.

G. Ethyl 1,6-dihydro-6-oxo-2-(3-trifluoromethylphenyl)pyrimidine-5-carboxylate, m.p. 151°-152°.

Anal. Calcd. for $C_{14}H_{11}F_3N_2O_3$: C, 53.85; H, 3.55; N, 8.97. Found: C, 53.84; H, 3.70; N, 8.71.

H. Ethyl 1,6-dihydro-6-oxo-2-(4-methoxyphenyl)pyrimidine-5-carboxylate, m.p. 230°-232°.

I. Ethyl 1,6-dihydro-6-oxo-2-(4-chlorophenyl)pyrimidine-5- carboxylate, m.p. 245°-247°.

Anal. Calcd. for $C_{13}H_{11}ClN_2O_3$: C, 56.02; H, 3.98; Cl, 12.72; Found: N, 10.05. Found: C, 55.94; H, 4.06; Cl, 12.46; N, 9.86.

J. Ethyl 1,6-dihydro-6-oxo-2-(4-trifluoromethylphenyl)-pyrimidine-5-carboxylate, m.p. 225°-226.5°.

Anal. Calcd. for $C_{14}H_{11}F_3N_2O_3$: C, 53.85; H, 3.55; N, 8.97 Found: C, 54.00; H, 3.62; N, 9.05.

Preparation 37: Ethyl 1,6-dihydro-6-oxo-2-(5-carbethoxy-2-ethoxyphenyl)-pyrimidine-5-carboxylate (benzamidine free base)

Diethyl ethoxymethylenemalonate (1.18 g., 5.45 mmoles) was added to a cold, stirred mixture of sodium ethoxide (0.37 g., 5.45 mmoles) and 5-carbomethoxy-2-ethoxy-benzamidine (1.21 g., 5.45 mmoles) in ethanol (15 ml.). The mixture was poured onto ice-water and acidified with acetic acid. The precipitate was recrystallized from ethanol to give the title compound (1.49 g., 76%) as colorless crystals, m.p. 180°-181.5°.

Note that during the coupling reaction between the carbomethoxybenzamidine and the ethoxymethylenemalonate, ester exchange occurs (under the influence of the NaOC₂H₅/C₂H₅OH) resulting in the 5'-carbethoxy product.

Preparation 38: Ethyl 1,6-dihydro-6-oxo-2-(5-amino-2-ethoxyphenyl)-pyrimidine-5-carboxylate A. Ethyl 1,6-dihydro-6-oxo-2-(2-ethoxy-5-nitrophenyl)-pyrimidine-5-carboxylate Ethyl 1,6-dihydro-6-oxo-2-(2-ethoxyphenyl)pyrimidine -5-carboxylate (1.0 g., 3,46 mmoles) was added over a twenty minute period to a cooled (ice-water), stirred mixture of 70% nitric acid (1.7 ml., d=1.42) and 96% sulfuric acid (0.29 ml., d=1.84). The mixture was stirred at room temperature for 19 hours. The solution was poured into ice-water (300 ml.). The mixture was triturated and then filtered. The collected solid was recrystallized from acetonitrile to give the title compound (0.64 g., 55%), m.p. 222-224°.

Anal. Calcd. for $C_{15}H_{15}N_3O_6$: C, 54.05; H, 4.54; N, 12.61. Found: C, 54.32; H, 4.71; N, 12.56.

B. Ethyl 1,6-dihydro-6:oxo-2-(5-amino-2-ethoxyphenyl)-pyrimidine-5-carboxylate

A mixture of ethyl 1,6-dihydro-6-oxo-2-(2-ethoxy-5-nitrophenyl)pyrimidine-5-carboxylate (0.42 g., 1.26 mmoles) and 10% palladium on carbon (0.07 g.) in ethanol (200 ml.) was treated with hydrogen at a pressure of about 3.5 kg./cm² until uptake of hydrogen ceased. The mixture was filtered and the filtrate reduced to dryness. The residue was recrystallized from water followed by aqueous ethanol to give the title compound (0.12 g., 31.6%), m.p. 107°-110°.

Anal. Calcd. for $C_{15}H_{17}N_3O_4 \cdot H_2O$: C, 56.07; N, 13.08; $H_2O$, 5.62. Found: C, 56.37; H, 5.70; N, 13.32; $H_2O$, 5.82.

Preparation 39: Ethyl 1,6-dihydro-6-pxp-2-(2-cyclopropylmethoxyphenyl)-pyrimidine-5-carboxylate The title compound was prepared from 2-cyclopropylmethoxybenzamidine hydrochloride in a manner similar to that described for the preparation of ethyl 1,6-dihydro-6-oxo-2- (2-allyloxyphenyl)pyrimidine-5-carboxylate in Preparation 29. The product had m.p. 104°-105°.

Anal. Calcd. for $C_{17}H_{18}N_2O_4$: C, 64.95; H, 5.77; N, 8.91. Found: C, 64.66; H, 5.93; N, 8.87.

Preparation 40: Ethyl 1,6-dihydro-6-oxo-2-(5-methoxy-2propoxyphenyl)-pyrimidine-5-carboxylate The title compound was prepared from 5-methoxy-2-n-propoxybenzamidine hydrochloride in a manner similar to that described for the preparation of ethyl 1,6-dihydro-6-oxo-2-(2-allyloxyphenyl)pyrimidine-5-carboxylate in Preparation 29. The product had m.p. 124°-126°.

Preparation 41: Ethyl 1,6-dihydro-6-oxo-2-(2,4-dimethoxyphenyl)pyrimidine-5-carboxylate A solution of diethyl ethoxymethylenemalonate (8.4 g., 0.0388 mole) in ethanol (20 ml.) was added dropwise to a cooled (ice-water) stirred mixture of 2,4-dimethoxybenzamidine (7.0 g., 0.0388 mole) in ethanol (50 ml.) containing sodium (0.89 g., 0.0388 g-atom). The mixture was heated under reflux for two hours. The cooled mixture was poured into ice-water and acidified with dilute hydrochloric acid. The precipitate was recrystallized from 95% ethanol to give ethyl 1,6-dihydro-6-oxo-2-(2,4-dimethoxyphenyl)pyrimidine-5-carboxylate (9.0 g., 63.5% yield), m.p. 190°-192°.

Anal. Calcd. for $C_{15}H_{16}N_2O_5$: C, 59.20; H, 1:; N, 9.21. Found: C, 59.15; H, 5.22; N, 9.19.

Preparation 42-1:

The following ethyl 1,6-dihydro-6-oxo-2-phenylpyrimidine-5-carboxylates were prepared from the reaction of the appropriate benzamidine with diethyl ethoxymethylenemalonate according to the general procedure of Preparation 41.

Ethyl 1,6-dihydro-6-oxo-2-(2-fluorophenyl)pyrimidine-5-carboxylate, m.p. 151°-153°.

Anal. Calcd. for $C_{13}H_{11}FN_2O_3$: C, 59.54; H, 4.23; N, 10.68.

Found: C, 59.69; H, 4.15; N, 11.05.

Ethyl 1,6-dihydro-6-oxo-2-(2-benzyloxyphenyl)pyrimidine-5-carboxylate, m.p. 156.5°-157.5°.

Anal. Calcd. for $C_{20}H_{18}N_2O_4$: C, 68.56; H, 5.18; N, 8.00.

Found: C, 68.27; H, 4.99; N, 8.01.

Preparation 42-2: Ethyl 1,6-Dihydro-6-oxo-2-(2-ethylthiophenyl)-pyrimidine-5-carboxylate 2-Ethylthiobenzamidine hydrochloride (2.12 g., 10.0 mmoles) was added to a cooled (ice-water) solution of sodium (0.46 g., 20 mg.-atoms) in ethanol (12 ml.). To this mixture was added a solution of diethyl ethoxymethylenemalonate (2.16 g., 10.0 mmoles) in ethanol (4 ml.). The mixture was heated under reflux for 3.5 hours. The cooled mixture was poured into ice-water (400 ml.) and acidified to pH 6 with glacial acetic acid. The precipitate was collected and recrystallized from acetonitrile to give the title compound (2.04 g., 64.6%), m.p. 117°-120°.

Anal. Calcd. for $C_{15}H_{16}N_2O_3S$: C, 59.19; H, 5.30; N, 9.20.

Found: C, 59.42; H, 5.31; N, 9.37.

Preparation 42-3: Ethyl 1,6-Dihydro-6-oxo-2-(2-methylthiophenyl)-pyrimidine-5-carboxylate In a manner similar to that described in Preparation 42-2, the title compound was prepared from 2-methylthiobenzamidine hydrochloride (disclosed in U.S. Pat. No. 3,819,631). After, recrystallization from benzene, the product has a m.p. 155°-156°.

Anal. Calcd. For $C_{14}H_{14}N_2O_3S$: C, 57.92; H, 4.86; N, 9.65; S, 11.04.

Found: C, 57.93; H, 4.76; N, 9.71; S, 11.01.

Preparation 42-4: Ethyl 1,6-Dihydro-6-oxo-2-(2-nitrophenyl)-pyrimidine-5-carboxylate Diethyl ethoxymethylenemalonate (0.73 g., 3.44 mmoles), potassium carbonate (0.95 g., 6.88 mmoles), and ethanol (11 ml.) were added to 2-nitrobenzamidine hydrochloride (0.69 g., 3.44 mmoles)(prepared according to general method disclosed in U.S. Pat. No. 2,450,386). The mixture was heated under reflux for 3.5 hours. The cooled mixture was filtered. The filtrate was poured into ice-water (150 ml.) and the pH adjusted to 6.0 with acetic acid. The precipitate was collected and dried to give the title compound (0.20 g., 20.2%), m.p. 171°–175°. Recrystallization from acetonitrile gave analytical material, m.p. 175°–177°.

Anal. Calcd. for $C_{13}H_{11}N_3O_5$: C, 53.98; H, 3.83; N, 14.53.

Found: C, 53.62; H, 3.90; N, 14.35.

Preparation 42-5: Ethyl 1,6-Dihydro-6-oxo-2-(2-aminophenyl)-pyrimidine-5-carboxylate A mixture of ethyl 1,6-dihydro-6-oxo-2-(2-nitrophenyl)pyrimidine-5-carboxylate (0.91 g., 3.14 mmoles), 10% palladium on carbon (0.34 g.) and ethanol (200 ml.) was shaken in an atmosphere of hydrogen at an initial pressure of 3.5 kg./cm². After hydrogen uptake ceased, the mixture was filtered and the filtrate concentrated. The residue was recrystallized from acetonitrile to give the title compound (0.445 g., 54.5%), m.p. 228°–230° (decomp.).

Anal. Calcd. for $C_{13}H_{13}N_3O_3$: C, 60.22; H, 5.05; N, 16.21.

Found: C, 59.89; H, 4.98; N, 16.51.

The 1,6-dihydro-6-oxo-2-phenylpyrimidine-5-carboxamides (general formula III) may be prepared as follows:

Preparation 43: 1,6-Dihydro-6-oxo-2-(2-ethoxyphenyl)pyrimidine-5-carboxamide A mixture of ethyl 1,6-dihydro-6-oxo-2-(2-ethoxyphenyl)pyrimidine-5-carboxylate (10.0 g.) and aqueous ammonia (120 ml., d = 0.90) was heated in a sealed vessel on a steam bath for 4.5 hours. The solution was partially evaporated and then acidified to pH 3 with 6N hydrochloric acid. The collected solid was washed with water, dried, and recrystallized from N,N-dimethylformamide to give the title compound (6.93 g., 77% yield), m.p. 236°–238°.

Anal. Calcd. for $C_{13}H_{13}N_3O_3$: C, 60.22; H, 5.05; N, 16.21.

Found: C, 60.15; H, 5.11; N, 15.77.

Preparation 44:

The following carboxamides were prepared from the corresponding ethyl 1,6-dihydro-6-oxo-2-phenylpyrimidine-5-carboxylates by the procedure described in Preparation 43 above.

A.
1,6-dihydro-6-oxo-2-(2-n-propoxyphenyl)pyrimidine-5-carboxamide, m.p. 225°–226°.

Anal. Calcd. for $C_{14}H_{15}N_3O_3$: C, 61.53; H, 5.53; N, 15.38.

Found: C, 61.76; H, 5.56; N, 15.14.

B.
1,6-dihydro-6-oxo-2-(2-methoxyphenyl)pyrimidine-5-carboxamide, m.p. 218°–219°.

Anal. Calcd. for $C_{12}H_{11}N_3O_3$: C, 58.77; H, 4.52; N, 17.14.

Found: C, 59.17; H, 4.48; N, 16.87.

C.
1,6-dihydro-6-oxo-2-(2-isopropoxyphenyl)pyrimidine-5-carboxamide, m.p. 200°–201°.

Anal. Calcd. for $C_{14}H_{15}N_3O_3$: C, 61.53; H, 5.53; N, 15.38.

Found: C, 61.42; H, 5.53; N, 14.99.

D.
1,6-dihydro-6-oxo-2-(2-n-butoxyphenyl)pyrimidine-5-carboxamide, m.p. 181°–183°.

Anal. Calcd. for $C_{15}H_{17}N_3O_3$: C, 62.70; H, 5.96; N, 14.63.

Found: C, 62.71; H, 5.94; N, 14.61.

Preparation 45: (±)-1,6-Dihydro-6-oxo-2-(2-sec-butoxyphenyl)-pyrimidine-5-carboxamide A steel bomb containing ethyl (±)-1,6-dihydro-6-oxo-2-(2-sec-butoxyphenyl)pyrimidine-5-carboxylate (3.76 g.) and liquid ammonia (ca. 45 ml.) was heated on a steam bath for four hours. The ammonia was removed. A solution of the residue in ice-water was acidified with concentrated hydrochloric acid. The precipitate was recrystallized from methanol to give the title compound (2.99 g., 87.7% yield), m.p. 183°–185°.

Anal. Calcd. for $C_{15}H_{17}N_3O_3$: C, 62.70; H, 5.96; N, 14.63.

Found: C, 62.37; H, 5.95; N, 14.50.

Preparation 46: 1,6-Dihydro-6-oxo-2-(2-isobutoxyphenyl)-pyrimidine-5-carboxamide A mixture of ethyl 1,6-dihydro-6-oxo-2-(2-isobutoxyphenyl)-pyrimidine-5-carboxylate (10.0 g., 0.0316 mole) and ammonium hydroxide (110 ml., d=0.9) was heated in a sealed steel bomb for 4.5 hours. The solution was partially evaporated and the residue acidified with 6N hydrochloric acid. The mixture was filtered and the collected solid recrystallized from N,N-dimethylformamide to give the title compound (7.5 g., 83% yield), m.p. 230°–231°.

Anal. Calcd. for $C_{15}H_{17}N_3O_3$: C, 62.70; H, 5.96; N, 14.63.

Found: C, 62.58; H, 5.91; N, 14.23.

Preparation 47: 1,6-Dihydro-6-oxo-2-(2-n-propoxyphenyl)-pyrimidine-5-carboxamide (illustrates use of NH₄OH at room temperature To a slurry of ethyl 1,6-dihydro-6-oxo-2-(2-n-propoxyphenyl)-pyrimidine-5-carboxylate (1811.4 g.) in ammonium hydroxide (12 l, d=0.9) was added tetrahydrofuran (800 ml.). The solution was stored at room temperature for 64 hours. Partial evaporation of the solvents under reduced pressure gave a thick slurry which was cooled and acidified to pH∼3 with 6N hydrochloric acid. The solid was collected by filtration, washed with water, dried, and recrystallized from N,N-dimethylformamide to give the title compound (1407.7 g., 86%), m.p. 227°–229°.

Preparation 48:

Following the general procedures of Preparations 43-47 above, there may be prepared from the appropriate ethyl 1,6-dihydro-6-oxo-2-phenylpyrimidine-5-carboxylates the following carboxamides:

A. 1,6-dihydro-6-oxo-2-(2-chlorophenyl)pyrimidine-5-carboxamide;
B. 1,6-dihydro-6-oxo-2-(3-methoxyphenyl)pyrimidine-5-carboxamide;
C. 1,6-dihydro-6-oxo-2-(3-trifluoromethyl)pyrimidine-5-carboxamide;
D. 1,6-dihydro-6-oxo-2-(4-methoxyphenyl)pyrimidine-5-carboxamide;
E. 1,6-dihydro-6-oxo-2-(4-trifluoromethyl)pyrimidine-5-carboxamide;
F. 1,6-dihydro-6-oxo-2-(2,4-dimethoxyphenyl)pyrimidine-5-carboxamide;
G. 1,6-dihydro-6-oxo-2-(2-fluorophenyl)pyrimidine-5-carboxamide;
H. 1,6-dihydro-6-oxo-2-(2-benzyloxyphenyl)pyrimidine-5-carboxamide;
I. 1,6-dihydro-6-oxo-2-(2-ethylthiophenyl)pyrimidine-5-carboxamide;
J. 1,6-dihydro-6-oxo-2-(2-methylthiophenyl)pyrimidine-5-carboxamide; and
K. 1,6-dihydro-6-oxo-2-(2-aminophenyl)pyrimidine-5-carboxamide.

Preparation 49:
1,6-Dihydro-6-oxo-2-(2-allyloxyphenyl)-pyrimidine-5-carboxamide

A mixture of ethyl 1,6-dihydro-6-oxo-2-(2-allyloxyphenyl)-pyrimidine-5-carboxylate (5.0 g.) and liquid ammonia (50 ml.) in a steel bomb was kept at 25° for 18 hours and then heated on a steam bath for 2.5 hours. The ammonia was removed. The residue was dissolved in water and the solution acidified with acetic acid. The precipitated title compound (4.4 g., 97%), m.p. 202–204° with resolodification and remelting at 275°–280°, was recrystallized from ethanol to give analytical material, m.p. 205°–207°.
Anal. Calcd. for $C_{14}H_{13}N_3O_3$: C, 61.98; H, 4.83; N, 15.49. Found: C, 61.97; H, 4.79; N, 15.30.

Preparation 50:
1,6-Dihydro-6-oxo-2-(2-cyclopropylemthoxyphenyl)-pyrimidine-5-carboxamide.

In a manner similar to that described for the preparation of 1,6-dihydro-6-oxo-2-(2-allyloxphenyl)pyrimidine-5-carboxamide in Preparation 49, the title compound was prepared from ethyl 1,6-dihydro-6-oxo-2-(2-cyclopropylmethoxyphenyl)pyrimidine-5-carboxylate. The product (100%) had m.p. 215°–217° (recrystallization from ethanol).
Anal. Calcd. for $C_{15}H_{15}N_3O_3$: C, 63.15; H, 5.30; N, 14.73. Found: C, 63.00; H, 5.46; N, 14.62.

Preparation 51:
1,6-Dihydro-6-oxo-2-(5-methoxy-2-n-propoxyphenyl)-pyrimidine-5-carboxamide A mixture of ethyl 1,6-dihydro-6-oxo-2-(5-methoxy-2-n-propoxyphenyl) pyrimidine-5-carboxylate (10.0 g.) and concentrated ammonium hydroxide (100 ml.) was heated in a sealed steel bomb on a steam bath for 4.5 hours. The reaction mixture was concentrated and then acidified to pH 3 with 6N hydrochloric acid. The collected solid was partially dried and recrystallized from acetonitrile to give the title compound (3.8 g., 41.6%), m.p. 206°–207°.
Anal. Calcd. for $C_{15}H_{17}N_3O_4$: C, 59.39; H, 5.65; N, 13.86. Found: C, 59.17; H, 5.81; N, 13.69.

The 1,6-dihydro-6-oxo-2-phenylpyrimidine-5-carbonitriles (general formula II) may be prepared according to the methods illustrated below.

Method A (via carboxamides)

Preparation 52:
1,6-Dihydro-6-oxo-2-(2-ethoxyphenyl)pyrimidine-5-carbonitrile

A solution of 1,6-dihydro-6-oxo-2-(2-ethoxyphenyl)pyrimidine-5-carboxamide (5.5 g.) in phosphorus oxychloride (160 ml.) was heated under reflux for 3.5 hours. The solution was evaporated under reduced pressure to a thick oil which was treated with water (150 ml.) with vigorous stirring. The mixture was filtered. The collected solid was washed with water, dried, and recrystallized from glacial acetic acid to give the title compound (3.48 g., 68% yield), m.p. 186°–187°.
Anal. Calcd. for $C_{13}H_{11}N_3O_2$: C, 64.72; H, 4.60; N, 17.42. Found: C, 65.09 H, 4.84; H, 17.75.

Preparation 53:

The following carbonitriles were prepared from the corresponding 1,6-dihydro-6-oxo-2-phenylpyrimidine-5-carboxamides by the procedure described in Preparation 52 above.

A.
1,6-dihydro-6-oxo-2-(2-n-propoxyphenyl)pyrimidine-5-carbonitrile, m.p. 171°–172°.
Anal. Calcd. for $C_{14}H_{13}N_3O_2$: C, 65.87; H, 5.13. Found: C, 65.82; H, 5.22.

B.
1,6-dihydro-6-oxo-2-(2-methoxyphenyl)pyrimidine-5-carbonitrile, m.p. 245°–246°.
Anal. Calcd. for $C_{12}H_9N_3O_2$: C, 63.43; H, 3.99; N, 18.49. Found: C, 63.09; H, 4.09; N, 18.22.

C.
1,6-dihydro-6-oxo-2-(2-isopropoxyphenyl)pyrimidine-5-carbonitrile, m.p. 174°–175°. Anal. Calcd. for $C_{14}H_{13}N_3O_2$: N, 16.46. Found: N, 16.53.

D.
1,6-dihydro-6-oxo-2-(2-butoxyphenyl)pyrimidine-5-carbonitrile, m.p. 171.5°–173.5°.
Anal. Calcd. for $C_{15}H_{15}N_3O_2$: C, 66.90; H, 5.61; N, 15.61. Found: C, 66.58; H, 5.62; N, 15.46.

(±)-1,6-dihydro-6-oxo-2-(2-sec-butoxyphenyl)pyrimidine-5-carbonitrile, m.p. 152°–158°.
Anal. Calcd. for $C_{15}H_{15}N_3O_2$: C, 66.90; H, 5.61; N, 15.61. Found: C, 66.59; H, 5.43; N, 15.77.

Preparation 54:
1,6-Dihydro-6-oxo-2-(2-isobutoxyphenyl)pyrimidine-5-carbonitrile A mixture of 1,6-dihydro-6-oxo-2-(2-isobutoxyphenyl)pyrimidine-5-carboxamide (7.4 g.) and phosphorus oxychloride (150 ml.) was heated under reflux for 3.5 hours. Excess phosphorus oxychloride was removed under reduced pressure. The residue was treated with water (150 ml.). The mixture was stirred briefly, cooled, and filtered. The collected solid was recrystallized from 50% aqueous acetic acid to give the title compound (3.9 g., 58% yield), m.p. 186°–187°.

Preparation 55:

Following the general procedures of Preparations 52-54 above, there may be produced from the appropriate 1,6-dihydro-6-oxo-2-phenylpyrimidine-5-carboxamides the following carbonitriles:

A. 1,6-dihydro-6-oxo-2-(2-chlorophenyl)pyrimidine-5-carbonitrile;
B. 1,6-dihydro-6-oxo-2-(3-methoxyphenyl)pyrimidine-5-carbonitrile;
C. 1,6-dihydro-6-oxo-2-(3-trifluoromethylphenyl)pyrimidine-5-carbonitrile;
D. 1,6-dihydro-6-oxo-2-(4-methoxyphenyl)pyrimidine-5-carbonitrile;
E. 1,6-dihydro-6-oxo-2-(4-trifluoromethyl)pyrimidine-5-carbonitrile;
F. 1,6-dihydro-6-oxo-2-(2,4-dimethoxyphenyl)pyrimidine-5-carbonitrile;
G. 1,6-dihydro-6-oxo-2-(2-fluorophenyl)pyrimidine-5-carbonitrile;
H. 1,6-dihydro-6-oxo-2-(2-benzyloxyphenyl)pyrimidine-5-carbonitrile;
I. 1,6-dihydro-6-oxo-2-(2-ethylthiophenyl)pyrimidine-5-carbonitrile;
J. 1,6-dihydro-6-oxo-2-(2-methylthiophenyl)pyrimidine-5-carbonitrile; and
K. 1,6-dihydro-6-oxo-2-(2-aminophenyl)pyrimidine-5-carbonitrile.

Preparation 56:
1,6-Dihydro-6-oxo-2-(2-allyloxyphenyl)pyrimidine-5-carbonitrile A solution of 1,6-dihydro-6-oxo-2-(2-allyloxyphenyl)pyrimidine-5-carboxamide (3.58 g.) in phosphorus oxychloride (60 ml.) was heated under reflux for 2 hours. The solution was evaporated to dryness. The residue was cooled in ice and then treated cautiously with ice-water. The mixture was warmed to 25° and then heated on a steam bath for 15 minutes. The solid was collected, washed with cold water, and recrystallized from benzene-Skellysolve B to give the title compound (2.3 g., 69%), m.p. 162°-164°.

Anal. Calcd. for $C_{14}H_{11}N_3O_2$: C, 66.39; H, 4.38; N, 16.59. Found: C, 66.36; H, 4.45; N, 16.53.

Preparation 57:
1,6-Dihydro-6-oxo-2-(2-cyclopropylmethoxyphenyl)pyrimidine-5-carbonitrile 1,6-Dihydro-6-oxo-2-(2-cyclopropylmethoxyphenyl)pyrimidine-5-carboxamide (13.6 g., 0.0476 mole) was added to a stirred, cold solution of pyridine (18.9 g., 0.24 mole) in phosphorus oxychloride (136 ml.), and the mixture heated under reflux for 15 minutes. The mixture was evaporated to dryness and the residue added to a mixture of ice and mthylene chloride. The mixture was neutralized with sodium bicarbonate. The methylene chloride layer was dried (sodium sulfate) and concentrated. To the residual oil was added 1N sodium hydroxide (15 ml.) and tetrahydrofuran (10 ml.). The mixture was allowed to stand at 25° for 18 hours. The mixture was washed with diethyl ether, filtered, and the filtrate acidified with acetic acid. The precipitate was recrystallized from toluene to give the title compound (7.6 g., 59.6%), m.p. 188°-190°. Two recrystallizations from ethyl acetate gave analytical material, m.p. 187°-189°.

Anal. Calcd. for $C_{15}H_{13}N_3O_2$: C, 67.40; H, 4.90; N, 15.72. Found: C, 67.00; H, 4.96; N, 15.50.

Preparation 58:
1,6-Dihydro-6-oxo-2-(5-methoxy-2-n-propoxyphenyl)pyrimidine-5-carbonitrile The title compound (82.5%), m.p. 192°-194°, recrystallized from 2-propanol, was prepared from 1,6-dihydro-6-oxo-2-(5-methoxy-2-n-propoxyphenyl)pyrimidine-5-carboxamide in a manner similar to that described in Preparation 56.

Anal. Calcd. for $C_{15}H_{15}N_3O_3$: C, 63.15; H, 5.30; N, 14.73. Found: C, 62.87; H, 5.28; N, 14.74.

Method B (via acrylate intermediates of formula VI)

Preparation 59:
1,6-Dihydro-6-oxo-2-(2-isopropoxyphenyl)-pyrimidine-5-carbonitrile A solution of ethyl 2-cyano-3-(2-isopropoxybenzamidino)acrylate (0.60 g., 1.99 mmoles) (prepared according to Preparation 60) in dimethyl sulfoxide (15 ml.) was heated by means of an oil bath maintained at 100° for 18 hours. The cooled mixture was poured into ice-water (400 ml.). The mixture was filtered to give the title compound (0.40 g., 78.7%), m.p. 182°-184°.

When the above procedure was repeated with toluene substituted for the dimethyl sulfoxide used therein, there was obtained the crude title product in 81.7% yield.

When the above procedure was repeated with N,N-dimethylformamide substituted for the dimethyl sulfoxide used therein, there was obtained the title product, m.p. 184°-188°, in 74% yield.

The acrylate intermediates of general formula VI may be prepared as follows:

Preparation 60: Ethyl 2-cyano-3-(2-isopropoxybenzamidino)acrylate

Ethyl ethoxymethylenecyanoacetate (0.95 g., 5.61 mmoles) was added to an ice-cold solution of 2-isopropoxybenzamidine (1.0 g., 5.61 mmoles) in ethanol (7.1 ml.). The mixture was stirred at 5° for 1.5 hours. The mixture was filtered to give the title compound (1.2 g., 71%), m.p. 118°-122°. An analytical sample has m.p. 123°'124° (decomp).

Anal. Calcd. for $C_{16}H_{19}N_3O_3$: C, 63.77; H, 6.36; N, 13.95. Found: C, 63.57; H, 6.25; N, 14.02.

In a similar manner, but substituting N,N-dimethylformamide for ethanol in the procedure above, ethyl 2-cyano-3-(2-isopropoxybenzamidino)acrylate, m.p. 118°-120°, was prepared in 76.2% yield.

EXAMPLE 1

2-(2-Ethoxyphenyl)-5-(5-1H-tetrazolyl)pyrimidin-4-(3H)-one

A mixture of 1,6-dihydro-6-oxo-2-(2-ethoxyphenyl)pyrimidine-5-carbonitrile (2.17 g., 9.0 mmole), sodium azide (0.645 g., 9.9 mmole), and ammonium chloride (0.53 g., 9.9 mmole) in dry, N,N-dimethylformamide (18 ml.) was stirred at 125° for 16 hours. The solvent was removed under reduced pressure. The residue was treated with water and the resulting slurry acidified with 1N hydrochloric acid. The mixture was filtered. The collected solid was washed with water, dried, and recrystallized from glacial acetic acid to give the title compound (1.28 g., 50% yield). An analytical sample had m.p. 289°-290° with decomposition.

Anal. Calcd. for $C_{13}H_{12}N_6O_2$: C, 54.92; H, 4.26; N, 29.57. Found: C, 55.09; H, 4.32; N, 29.29.

EXAMPLE 2

2-(2-n-Propoxyphenyl)-5-(5-1H-tetrazolyl)pyrimidin-4(3H)-one

The procedure of Example 1 is repeated except than an equimolar amount of 1,6-dihydro-6-oxo-2-(2-n-propoxyphenyl)-pyrimidine-5-carbonitrile is used in place of the 1,6-dihydro-6-oxo-2-(2-ethoxyphenyl)-pyrimidine-5-carbonitrile used therein. There is produced the title product, m.p. 247°–248°.

Anal. Calcd. for $C_{14}H_{14}N_6O_2$: N, 28.17. Found: N, 28.27.

EXAMPLE 3

2-(2-Isopropoxyphenyl)-5-(5-1H-tetrazolyl)pyrimidin-4(3H)-one

The procedure of Example 1 is repeated except than an equimolar amount of 1,6-dihydro-6-oxo-2-(2-isopropoxyphenyl)pyrimidine-5-carbonitrile is used in place of the 1,6-dihydro-6-oxo-2-(2-ethoxyphenyl)-pyrimidine-5-carbonitrile used therein. There is produced the title product, m.p. 275°–276° with decomposition.

Anal. Calcd. for $C_{14}H_{14}N_6O_2$: C, 56.37; H, 4.73; N, 28.17. Found: C, 56.22; H, 4.75; N, 28.13.

EXAMPLE 4

2-(2-n-Butoxyphenyl)-5-(5-1H-tetrazolyl)pyrimidin-4(3H)-one

The procedure of Example 1 is repeated except that an equimolar amount of 1,6-dihydro-6-oxo-2-(2-n-butoxyphenyl)pyrimidine-5-carbonitrile is used in place of the 1,6-dihydro-6-oxo-2-(2-ethoxyphenyl)pyrimidine-5-carbonitrile used therein. There is produced the title product, m.p. 244°–247° with decomposition.

Anal. Calcd. for $C_{15}H_{16}N_6O_2$: C, 57.68; H, 5.16; N, 26.91. Found: C, 57.41; H, 5.13; N, 27.09.

EXAMPLE 5

($\pm$)-2-(2-sec-Butoxyphenyl)-5-(5-1H-tetrazolyl)pyrimidin-4(3H)-one

The procedure of Example 1 is repeated except that an equimolar amount of ($\pm$)-1,6-dihydro-6-oxo-2-(2-sec-butoxyphenyl)pyrimidine-5-carbonitrile is used in place of the 1,6-dihydro-6-oxo-2-(2-ethoxyphenyl)-pyrimidine-5-carbonitrile used therein. There is produced the title product, m.p. 240°–242° with decomposition. It should be noted that the product of this example contains an asymmetric carbon atom and thus can exist as the racemate, i.e. equal mixtures of the (+) and (−) optical isomers or, upon resolution by methods known per se, as the individual (+) and (−) isomers.

Anal. Calcd. for $C_{15}H_{16}N_6O_2$: C, 57.68; H, 5.16; N, 26.91. Found: C, 57.49; H, 5.09; N, 26.66.

EXAMPLE 6

2-(2-Methoxyphenyl)-5-(5-1H-tetrazolyl)pyrimidin-4(3H)-one

Sodium azide (283 mg., 4.35 mmole) was added to a solution of aluminum chloride (193 mg., 1.45 mmole) in tetrahydrofuran (8 ml.). The mixture was stirred under reflux for 0.5 hours. 1,6-Dihydro-6-oxo-2-(2-methoxyphenyl)pyrimidine-5-carbonitrile (300 mg., 1.32 mmole) was then added and the mixture stirred under reflux for 24 hours. The cooled mixture was diluted with water (15 ml.) and acidified with 6N hydrochloric acid. The mixture was filtered. The collected solid was recrystallized from glacial acetic acid to give the title compound (130 mg., 36.4% yield), m.p. 282°–283° with decomposition. Anal. Calcd. for $C_{12}H_{10}N_6O_2$: C, 53.33; H, 3.73; N, 31.10. Found: C, 53.20; H, 3.74; N, 31.50.

EXAMPLE 7

2-(2-Isobutoxyphenyl)-5-(5-1H-tetrazolyl)pyrimidin-4(3H)-one

A mixture of 1,6-dihydro-6-oxo-2-(2-isobutoxyphenyl)-pyrimidine-5-carbonitrile (3.78 g., 0.014 mole), sodium azide (1.0 g., 0.0154 mole), and ammonium chloride (0.824 g., 0.0154 mole) in N,N-dimethylformamide was heated at 125° for 19 hours stirring. The solvent was removed under reduced pressure. The residue was treated with water (40 ml.). The mixture was acidified with 6N hydrochloric acid with stirring. The mixture was filtered and the collected solid recrystallized from glacial acetic acid to give the title compound (2.4 g., 55% yield), m.p. 230°–231°.

Anal. Calcd. for $C_{15}H_{16}N_6O_2$: C, 57.68; H, 5.16; N, 26.91. Found: C, 57.52; H, 5.27; N, 26.72.

EXAMPLE 8

2-(2-Allyloxyphenyl)-5-(5-1H-tetrazolyl)pyrimidin-4(3H)-one

Aluminum chloride (1.71 g., 0.0128 mole) followed by sodium azide (2.5 g., 0.0384 mole) was cautiously added to ice-cold, stirred tetrahydrofuran (100 ml.). The mixture was heated under reflux for 0.5 hour. To the mixture was added 1,6-dihydro-6-oxo-2-(2-allyloxyphenyl)pyrimidine-5-carbonitrile (3.23 g., 0.0128 mole) and refluxing was continued for 18 hours. The cooled reaction mixture was diluted with water and acidified with 6N hydrochloric acid. The precipitate was collected and recrystallized from 95% ethanol to give the title compound (1.4 g., 37%), m.p. 221°–225°. Two recrystallizations from acetic acid gave analytical material, m.p. 230.5°–232° (decomp).

Anal. Calcd. for $C_{14}H_{12}N_6O_2$: C, 56.75; H, 4.08, N, 28.37. Found: C, 56.71; H, 4.24, N, 28.40.

EXAMPLE 9

2-(2-Cyclopropylmethoxyphenyl)-5-(5-1H-tetrazolyl)-pyrimidin-4(3H)-one

A stirred mixture of 1,6-dihydro-6-oxo-2-(2-cyclopropyl-methoxyphenyl)pyrimidine-5-carbonitrile (4.5 g., 0.0168 mole), sodium azide (1.2 g., 0.0184 mole) and ammonium chloride (0.99 g., 0.0185 mole) in N,N-dimethylformamide (45 ml.) was heated by means of an oil bath maintained at 125° for 20 hours. The mixture was concentrated. The residue was diluted with water and the mixture acidified with concentrated hydrochloric acid. The precipitated title compound (4.7 g., 90%), m.p. 237°–243° (decomp), was recrystallized from acetic acid followed by 2-methoxyethanol to give analytical material, m.p. 252°–254° (decomp).

Anal. Calcd. for $C_{15}H_{14}N_6O_2$: C, 58.05; H, 4.55; N, 27.09. Found: C, 58.16; H, 4.66; N, 27.04.

EXAMPLE 10

2-(5-Methoxy-2-n-propoxyphenyl)-5-(5-1H-tetrazolyl)-pyrimidin-4(3H)-one

In a manner similar to that described for the preparation of 2-(2-cyclopropylmethoxyphenyl)-5-(5-1H-tetrazolyl)pyrimidin-4(3H)-one in Example 9, the title compound was prepared from 1,6-dihydro-6-oxo-2-(5-methoxy-2-n-propoxyphenyl)pyrimidine-5-carbonitrile. The crude product was recrystallized from 2-methoxyethanol to give analytical material (65%), m.p. 257°-260°.

Anal. Calcd. for $C_{15}H_{16}N_6O_3$: C, 54.87; H, 4.91; N, 25.60. Found: C, 54.92; H, 4.90; N, 25.69.

Example 11

2-(2-Isopropoxyphenyl)-5-(5-1H-tetrazolyl)pyrimidin-4(3H)-one (via acrylate intermediate)

To a solution of ethyl 2-cyano-3-(2-isopropoxybenzamidino)-acrylate (0.60 g., 1.99 mmoles) in N,N-dimethylformamide (15 ml.) was added sodium azide (0.159 g., 2.44 moles) and ammonium chloride (0.131 g., 2.44 mmoles). The mixture was heated at 127° for 21 hours. The cooled mixture was poured into ice-water (400 ml.) and acidified to pH 2 with 6N hydrochloric acid. The mixture was filtered and the collected solid recrystallized from 2-methoxyethanol to give the title compound (0.06 g., 10%), m.p. 274°-277°.

EXAMPLE 12

2-(2-n-Propoxyphenyl)-5-(5-1H-tetrazolyl)pyrimidin-4(3H)-one (illustrates single step procedure)

To a cooled (ice bath) solution of 2-n-propoxybenzamide (1.00 g., 5.61 mmoles) in dry N,N-dimethylformamide (4 ml.) was added ethyl ethoxymethylenecyanoacetate (0.94 g., 5.61 mmoles). Twenty minutes later sodium azide (0.447 g., 6.88 mmoles) and ammonium chloride (0.368 g., 6.88 mmoles were added. The ice bath was removed and the mixture heated by means of an oil bath maintained at 127° for 30 hours. The cooled mixture was poured into ice-water (400 ml.) and acidified with 6N hydrochloric acid. The collected solid (0.93 g.), m.p. 245°-248° (decomp) was recrystallized from 2-methoxyethanol to give the title compound (0.69 g., 41%) m.p. 256°-257° (decomp).

EXAMPLE 13

2-(2-Isopropoxyphenyl)-5-(5-1H-tetrazolyl)pyrimidin-4(3H)-one (single step procedure)

By replacing 2-n-propoxybenzamidine in Example 12 with 2-isopropoxybenzamidine, the title compound was prepared in a similar manner. The recrystallized product (38%) had m.p. 282°-283° (decomp).

EXAMPLE 14

2-(5-Nitro-2-n-propoxyphenyl)-5-(5-1H tetrazolyl)pyrimidin-4(3H)-one 2-(2-n-Propoxyphenyl)-5-(5-1H-tetrazolyl)pyrimidin-4(3H)-one (1.03 g., 3.46 mmoles) was added over a period of 20 minutes to a cooled (5°) mixture of 70% nitric acid (1.7 ml., 26.9 mmoles) and concentrated sulfuric acid (2 ml.). The mixture was allowed to stand at room temperature for 2 hours. The mixture was poured onto ice-water (200 ml.). The precipitate was recrystallized from 2-methoxyethanol to give the title compound (0.73 g., 61.3%), m.p. 251°-252° (decomp).

Anal. Calcd. for $C_{14}H_{13}N_7O_4$: C, 48.98; H, 3.82; N, 28.56. Found: C, 48.76; H, 3.71; N, 28.47.

EXAMPLE 15

2-(5-Amino-2-n-propoxyphenyl)-5-(5-1H-tetrazolyl)-pyrimidin-4(3H)-one

A mixture of 2-(5-nitro-2-n-propoxyphenyl)-5-(5-1H-tetrazolyl)pyrimidine-4(3H)-one (5.0 g.) and 10% paladium-on-carbon (4.0 g.) in 2-methoxyethanol (900 ml.) was shaken in an atmosphere of hydrogen at an initial pressure of 3.5 kg./cm$^2$ for 19 hours. The mixture was filtered and the filtrate evaporated to dryness to give the title compound (3.6 g., 79%), m.p. 250°-253° (decomp). Recrystallization from 2-methoxyethanol gave analytical material, m.p. 261°-262°.

Anal. Calcd. for $C_{14}H_{15}N_7O_2$: C, 53.66; H, 4.83. Found: C, 53.92; H, 5.04.

EXAMPLE 16

2-(5-Dimethylamino-2-n-propoxyphenyl)-5-(5-1H-tetrazolyl)pyrimidin-4(3H)-one

To a suspension of 2-(5-amino-2-n-propoxyphenyl)-5-(5-1H-tetrazolyl)pyrimidin-4(3H)-one (0.50 g., 1.6 mmoles) in acetonitrile (40 ml.) was added 37% formaldehyde in water (1.32 ml., 16.0 mmoles). Sodium cyanoborohydride (0.302 g., 4.8 mmoles) was then added followed by glacial acetic acid (1.67 ml. The suspension was stirred at room temperature for 15 minutes and then heated under reflux for 3 hours. The mixture was cooled in an icebath. The precipitate was recrystallized from acetonitrile to give the title compound (0.19 g., 35%), m.p. 258°-259°.

Anal. Calcd. for $C_{16}H_{19}N_7O_2$: C, 56.29; H, 5.61; N, 28.73. Found: C, 55.92; H, 5.42; N, 28.63.

EXAMPLE 17

Following the general procedures of Examples 1-16, the following compounds may be prepared by use of the appropriate nitrile starting material. The nitriles are either disclosed in Preparations 52-59 above or are made following the general methods illustrated therein.

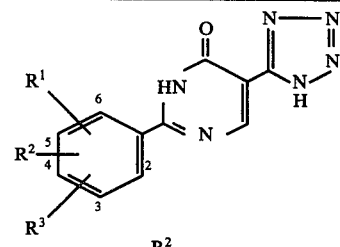

| R$^1$ | R$^2$ | R$^3$ |
|---|---|---|
| 2-Cl | H | H |
| 3-OCH$_3$ | H | H |
| 3-CF$_3$ | H | H |
| 4-OCH$_3$ | H | H |
| 4-Cl | H | H |
| 4-CF$_3$ | H | H |
| 2-F | H | H |
| 2-OCH$_2$C$_6$H$_5$ | H | H |
| 2-OH | H | H |
| 2-CH$_3$ | H | H |
| 2-C$_2$H$_5$ | H | H |
| 2-C$_3$H$_7$ | H | H |
| 2-CH$_2$CH=CH$_2$ | H | H |
| 2-CH=CH$_2$ | H | H |
| 2-cyclopropyloxy | H | H |
| 2-OCH$_2$OCH$_3$ | H | H |
| 2-OCH$_2$CH$_2$OCH$_3$ | H | H |
| 2-CF$_3$ | H | H |
| 2-OCF$_3$ | H | H |
| 2-OCH$_2$CF$_3$ | H | H |
| 2-SCH$_3$ | H | H |
| 2-SC$_2$H$_5$ | H | H |

4,082,751

-continued

Structure: Phenyl ring (with R¹ at position 6, R² at positions 4/5, R³ at position 3, and a substituent at position 2) connected via C(=N-)- to -NH-C(=O)-CH=CH-tetrazole.

| R¹ | R² | R³ |
|---|---|---|
| 4-morpholinyl (—N(morpholine)) | H | H |
| 1-pyrrolidinyl (—N(pyrrolidine)) | H | H |
| 1-piperidinyl (—N(piperidine)) | H | H |
| 2-NH₂ | H | H |
| 2-NHCH₃ | H | H |
| 2-NHC₂H₅ | H | H |
| 2-N(CH₃)₂ | H | H |
| 2-COOH | H | H |
| 2-CO₂CH₃ | H | H |
| 2-CO₂C₂H₅ | H | H |
| 2-OCH₂CO₂H | H | H |
| 2-OCH₂CO₂CH₃ | H | H |
| 2-O—C(=O)—NHCH₃ | H | H |
| 2-C(=O)CH₃ | H | H |
| 2-C(=O)—C₂H₅ | H | H |
| 2-NH—C(=O)—CH₃ | H | H |
| 2-NH—C(=O)—C₆H₅ | H | H |
| 2-O—C(=O)—CH₃ | H | H |
| 2-O—C(=O)—CH₂C₆H₅ | H | H |
| 2-O—C(=O)—C₆H₅ | H | H |
| 2-OCH₂CH₂OH | H | H |
| 2-OCH₂—CH(OH)—CH₂OH | H | H |
| 2-OCH₂—CH(OH)—CH₂OCH₃ | H | H |
| 2-OCH₂CH₂CH₂OH | H | H |
| 2-OCH₃ | 4-OCH₃ | H |
| 3-CH₃ | 4-CH₃ | H |
| 2-Cl | 5-Cl | H |
| 2-F | 5-F | H |
| 3-OCH₃ | 4-OCH₃ | H |
| 2-O-n-C₃H₇ | 5-Cl | H |
| 2-O-n-C₃H₇ | 5-F | H |
| 2-O-n-C₃H₇ | 5-CH₃ | H |
| 2-O-n-C₃H₇ | 5-C₂H₅ | H |
| 2-O-n-C₃H₇ | 5-CH₂CH=CH₂ | H |
| 2-O-n-C₃H₇ | 5-CH=CH₂ | H |
| 2-O-n-C₃H₇ | 5-OC₂H₅ | H |
| 2-O-n-C₃H₇ | 5-O-n-C₃H₇ | H |
| 2-O-n-C₃H₇ | 5-OCH(CH₃)₂ | H |
| 2-O-n-C₃H₇ | 5-OCH₂CH=CH₂ | H |
| 2-O-n-C₃H₇ | 5-OCH₂CH₂OCH₃ | H |
| 2-O-n-C₃H₇ | 5-CF₃ | H |
| 2-O-n-C₃H₇ | 5-OCF₃ | H |
| 2-O-n-C₃H₇ | 5-OCH₂CF₃ | H |
| 2-O-n-C₃H₇ | 5-OH | H |
| 2-O-n-C₃H₇ | 5-SCH₃ | H |
| 2-O-n-C₃H₇ | 5-NHCH₃ | H |
| 2-O-n-C₃H₇ | 5-N(morpholinyl) | H |
| 2-O-n-C₃H₇ | 5-N(pyrrolidinyl) | H |
| 2-O-n-C₃H₇ | 5-N(piperidinyl) | H |
| 2-O-n-C₃H₇ | 5-NHC₂H₅ | H |
| 2-O-n-C₃H₇ | 5-COOH | H |
| 2-O-n-C₃H₇ | 5-CO₂CH₃ | H |
| 2-O-n-C₃H₇ | 5-CO₂C₂H₅ | H |
| 2-O-n-C₃H₇ | 5-OCH₂CO₂H | H |
| 2-O-n-C₃H₇ | 5-OCH₂CO₂CH₃ | H |
| 2-O-n-C₃H₇ | 5-O—C(=O)—NHCH₃ | H |
| 2-O-n-C₃H₇ | 5-C(=O)—CH₃ | H |
| 2-O-n-C₃H₇ | 5-C(=O)—C₂H₅ | H |
| 2-O-n-C₃H₇ | 5-NH—C(=O)—CH₃ | H |
| 2-O-n-C₃H₇ | 5-NH—C(=O)—C₆H₅ | H |
| 2-O-n-C₃H₇ | 5-O—C(=O)—CH₃ | H |
| 2-O-n-C₃H₇ | 5-O—C(=O)—CH₂C₆H₅ | H |
| 2-O-n-C₃H₇ | 5-O—C(=O)—C₆H₅ | H |
| 2-O-n-C₃H₇ | 5-OCH₂CH₂OH | H |
| 2-O-n-C₃H₇ | 5-OCH₂—CH(OH)—CH₂OH | H |
| 2-O-n-C₃H₇ | 5-OCH₂—CH(OH)—CH₂OCH₃ | H |
| 2-O—CH(CH₃)₂ | 5-OCH₃ | H |
| 2-O—CH(CH₃)₂ | 5-OC₂H₅ | H |
| 2-O—CH(CH₃)₂ | 5-O-n-C₃H₇ | H |
| 2-O—CH(CH₃)₂ | 5-OCH(CH₃)₂ | H |
| 2-O—CH(CH₃)₂ | 5-OCH₂CH=CH₂ | H |
| 2-O—CH(CH₃)₂ | 5-CF₃ | H |
| 2-OC₂H₅ | 5-OCH₃ | H |
| 2-OC₂H₅ | 5-OC₂H₅ | H |
| 2-OC₂H₅ | 5-O-n-C₃H₇ | H |
| 2-OC₂H₅ | 5-OCH(CH₃)₂ | H |
| 2-O-n-C₄H₉ | 5-OC₂H₅ | H |
| 2-O-n-C₄H₉ | 5-O-n-C₃H₇ | H |
| 2-O-n-C₄H₉ | 5-OCH(CH₃)₂ | H |
| 3-OCH₃ | 4-OCH₃ | 5-OCH₃ |

EXAMPLE 18

2-(2-n-Propoxyphenyl)-5-(5-1H-tetrazolyl)pyrimidin-4(3H)-one Sodium Salt

A slurry of 2-(2-n-propoxyphenyl)-5-(5-1H-tetrazolyl)-pyrimidin-4(3H)-one (298 mg., 1 mmole) in water (10 ml.) was treated with 1N sodium hydroxide (1 ml.). The resulting solution was filtered. The filtrate was reduced in volume and treated with acetone. The slurry was stirred for 20 minutes. The sodium salt was collected by filtration, washed with acetone, dried, and allowed to stand exposed to the atmosphere for 1 week.

Anal. Calcd. for $C_{14}H_{13}N_6NaO_2.2H_2O$: C, 47.19; H, 4.81; N, 23.59; $H_2O$, 10.11. Found: C, 47.37; H, 4.55; N, 24.54; $H_2O$, 11.70.

Replacement of the 2-(2-n-propoxyphenyl)-5-(5-1H-tetrazolyl)pyrimidin-4-(3H)-one in the above procedure with an equimolar weight of the other 5-(5-1H-tetrazoly)pyrimidin-4(3H)-one compounds prepared in Examples 1, 3-11, and 3-17 above gives the corresponding sodium salts for each of the named compounds.

Replacement of the sodium hydroxide in the above procedure with other bases, e.g. KOH, $Ca(OH)_2$, $Mg(OH)_2$, or $NH_4OH$, gives the corresponding base addition salts.

The 5-(5-1H-tetrazolyl)pyrimidin-4(3H)-one compounds prepared in Examples 1–17 may be converted to their acid addition salts by addition of a stoichiometric equivalent of a suitable acid, e.g. HCl, HBr, HI, $CH_3COOH$ or $H_3PO_4$, to a methanolic solution of the desired pyrimidin-4(3H)-one compound.

EXAMPLE 19

Ethanolamine Monohydrate Salt of 2-(2-n-Propoxyphenyl)-5-(5-1H-tetrazolyl)pyrimidin-4(3H)-one Freshly distilled ethanolamine (141.6 g., 2.32 moles) was added to a stirred suspension of micropulverized 2-(2-n-propoxyphenhl)-5-(5-1H-tetrazolyl)pyrimidin-4(3H)-one (671.4 g., 2.25 moles) in distilled water (7 l). Stirring was continued at 40° to effect almost total solution. The mixture was filtered and the filtrate lyophilized to leave the title compound (831.4 g., 98%), m.p. 145°–148°.

Anal. Calcd. for $C_{14}H_{14}N_6O_2.C_2H_7NO.H_2O$ : C, 50.92; H, 6.14; N, 25.98; $H_2O$, 4.77. Found: C, 50.71; H, 6.09; N, 26.18; $H_2O$, 5.64.

EXAMPLE 20

Ethylenediamine Dihydrate Salt of 2-(2-n-Propoxyphenyl)-5-(5-1H-tetrazolyl)pyrimidin-4(3H)-one Ethylenediame (0.625 g., 0.0104 mole) was added to a stirred suspension of 2-(2-n-propoxyphenyl)-5-(5-1H-tetrazolyl)-pyrimidin-4(3H)-one (2.98 g., 0.010 mole) in water (30 ml.). Total solution was obtained upon gentle warming. The solution was lyophilized to leave a quantitative yield of the title compound m.p. 177°–180°, which was allowed to equilibrate with atmoshperic moisture for one month.

Anal. Calcd. for $C_{14}H_{14}N_6O_2.C_2H_8N_2$. $2H_2O$: C, 48.72; H, 6.64; N, 28.41; $H_2O$, 9.13. Found: C, 48.98; H, 6.21; N, 29.25; $H_2O$, 8.75.

EXAMPLE 21

Following the general procedures of Example 19, but substituting diethanolamine, triethanolamine and tris(hydroxymethyl)-aminomethane for the ethanolamine used therein, the following water soluble salts of 2-(2-n-propoxyphenyl)-5-(5-1H-tetrazolyl)-pyrimidin-4(3H)-one were prepared;

diethanolamine salt, $C_{14}H_{14}N_6O_2$. $C_4H_{11}NO_2$, m.p. 138°–143° triethanolamine salt, $C_{14}H_{14}N_6O_2.C_6H_{15}NO_3$, m.p. 146°–199° tris(hydroxymethyl)aminomethane salt, $C_{14}H_{14}N_6O_2.C_4H_{11}NO_3$, m.p. 180°–195°

Replacement of the 2-(2-n-propoxyphenyl)-5-(5-1H-tetrazolyl)pyrimidin-4(3H)-one in the procedures of Examples 19–21 with an equimolar weight of the other 5-(5-1H-tetrazolyl)pyrimidin-4(3H)-one compounds prepared in Examples 1,3–11, and 13–17 gives the corresponding salts for each of the named compounds.

We claim:

1. A compound of the formula

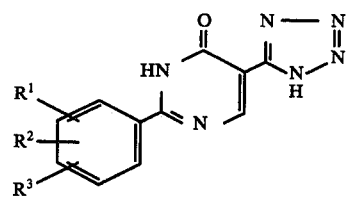

wherein $R^1$, $R^2$ and $R^3$ which may be the same or different are each hydrogen, halogen, (lower)alkyl, (lower)alkenyl, (lower)alkoxy, —O—(lower)alkenyl,

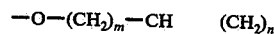

in which $m$ is 0 or an integer from 1 to 6 and $n$ is an integer from 2 to 7, $-OCH_2(CH_2)_xO(CH_2)_yCH_3$ in which $x$ is 0 or an integer from 1 to 6 and $y$ is 0 or an integer from 1 to 6, $CF_3$, $-OCF_3$, $-OCH_2CF_3$, hydroxy, (lower)alkylthio, amino, nitro,

in which $r$ is 4 or 5, (lower)-alkylamino, di(lower)alkylamino, carboxyl, $-CO_2$—(lower)alkyl, $-O(CH_2)_uu CO_2-R^a$ in which $u$ is an integer from 1 to 6 and $R^a$ is hydrogen or (lower)alkyl, $R^c$—CO— in which $R^c$ is (lower)alkyl, $R^c$—CONH— in which $R^c$ is (lower) alkyl, $R^c$—COO— in which $R^c$ is (lower)alkyl,

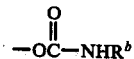

in which $R^b$ is (lower)alkyl, $-O(CH_2)_kOH$ in which $k$ is an integer from 2 to 6,

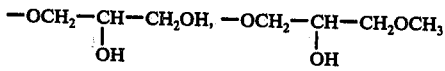

or $-OCH_2C_6H_5$, and pharmaceutically acceptable salts thereof, with the proviso that $R^1$, $R^2$ and $R^3$ may not all be alike except in the case where they represent (lower)-alkoxy.

2. A compound of the formula

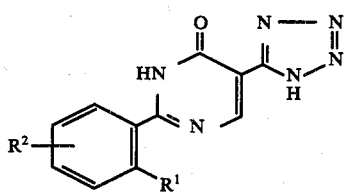

wherein $R^1$ and $R^2$ which may be the same or different are each hydrogen, halogen, (lower)alkyl, (lower)alkenyl, (lower)alkoxy, —O—(lower)alkenyl,

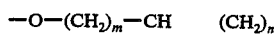

in which m is 0 or an integer from 1 to 6 and n is an integer from 2 to 7, —OCH$_2$-(CH$_2$)$_x$O(CH$_2$)$_y$CH$_3$ in which x is 0 or an integer from 1 to 6 and y is 0 or an integer from 1 to 6, CF$_3$, —OCF$_3$, —OCH$_2$CF$_3$, hydroxy, (lower)alkylthio, amino, nitro,

in which r is 4 or 5, (lower)-alkylamino, di(lower)alkylamino, carboxyl, —CO$_2$—(lower)alkyl, —O(CH$_2$)$_u$CO$_2$—R$^a$ in which u is an integer from 1 to 6 and R$^a$ is hydrogen or (lower)alkyl, R$^c$—CO— in which R$^c$ is (lower)alkyl, R$^c$—CONH— in which R$^c$ is (lower)alkyl, R$^c$—CONH— in which R$^c$ is (lower)alkyl,

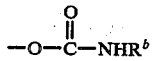

in which R$^b$ is (lower)alkyl, —O(CH$_2$)$_k$OH in which k is an integer from 2 to 6,

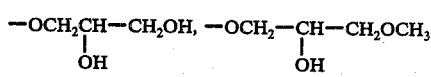

or —OCH$_2$C$_6$H$_5$, or a pharmaceutically acceptable salt thereof, with the proviso that $R^1$ is never hydrogen.

3. A compound of the formula

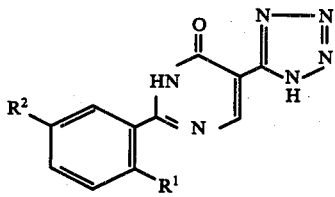

wherein $R^1$ and $R^2$ which may be the same or different are each hydrogen, halogen, (lower)alkyl, (lower)alkenyl, (lower)alkoxy, —O—(lower)alkenyl,

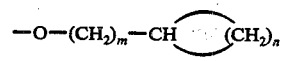

in which m is 0 or an integer from 1 to 6 and n is an integer from 2 to 7, —OCH$_2$(CH$_2$)$_x$O(CH$_2$)$_y$CH$_3$ in which x is 0 or an integer from 1 to 6 and y is 0 or an integer from 1 to 6, CF$_3$, —OCF$_3$, —OCH$_2$CF$_3$, hydroxy, (lower)alkylthio, amino, nitro,(lower)-alkylamino, di(lower)alkylamino,

in which r is 4 or 5, carboxyl, —CO$_2$—(lower)alkyl, —O(CH$_2$)$_u$CO$_2$R$^a$ in which u is an integer from 1 to 6 and R$^a$ is hydrogen or (lower)alkyl, R$^c$—CO— in which R$^c$ is (lower)alkyl, R$^c$—CONH— in which R$^c$ is (lower)alkyl, R$^c$—COO— in which R$^c$ is (lower)-alkyl,

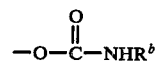

in which R$^b$ is (lower)alkyl, —O(CH$_2$)$_k$OH in which k is an integer from 2 to 6,

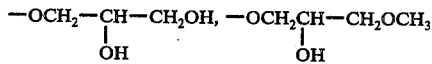

or —OCH$_2$C$_6$H$_5$, or a pharmaceutically acceptable salt thereof, with the proviso that $R^1$ is never hydrogen.

4. A compound of the formula

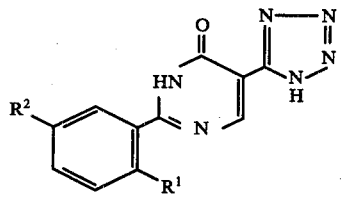

wherein $R^1$ is (lower)alkoxy, —O—(lower)alkenyl or

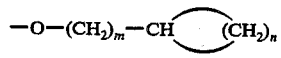

in which m is 0 or an integer from 1 to 6 and n is an integer from 2 to 7 and $R^2$ is hydrogen, halogen, (lower)alkyl, (lower)alkenyl, (lower)alkoxy, —O—(lower)alkenyl,

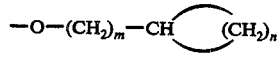

in which m is 0 or an integer from 1 to 6 and n is an integer from 2 to 7, —OCH$_2$(CH$_2$)$_x$O(CH$_2$)$_y$CH$_3$ in which x is 0 or an integer from 1 to 6 and y is 0 or an integer from 1 to 6, CF$_3$, —OCF$_3$, —OCH$_2$CF$_3$, hydroxy, (lower)alkylthio, amino, nitro,

—N(CH₂)ᵣ in which r is 4 or 5, (lower)alkylamino, di(lower)alkylamino, carboxyl, —CO₂—(lower)alkyl, —O(CH₂)ᵤCO₂Rᵃ in which u is an integer from 1 to 6 and Rᵃ is hydrogen or (lower)alkyl, Rᶜ—CO—in which Rᶜ is (lower)alkyl, Rᶜ—CONH— in which Rᶜ is (lower)alkyl, Rᶜ—COO— in which Rᶜ is (lower)alkyl, $$-O-\overset{O}{\underset{\|}{C}}-NHR^b$$

in which Rᵇ is (lower)alkly, —O(CH₂)ₖOH in which k is an integer from 2 to 6,

—OCH₂—CH—CH₂OH, —OCH₂CH—CH₂OCH₃
        |                   |
        OH              OH or —OCH₂C₆H₅, or a pharmaceutically acceptable salt thereof.

5. A compound of claim 4 wherein R¹ is —O—C₁—C₆ alkyl, or a pharmaceutically acceptable salt thereof.

6. A compound of claim 5 wherein R¹ is methoxy, ethoxy, n-propoxy, isopropoxy, n-butoxy, isobutoxy or sec-butoxy, or a pharmaceutically acceptable salt thereof.

7. A compound of claim 4 wherein R¹ is —O—C₂—C₆ alkenyl, or a pharmaceutically acceptable salt thereof.

8. A compound of claim 7 wherein R¹ is allyloxy, or a pharmaceutically acceptable salt thereof.

9. A compound of claim 4 wherein R¹ is

—O—(CH₂)ₘ—CH⟨(CH₂)ₙ⟩ in which m is 0 or an integer from 1 to 4 and n is an integer from 2 to 5, or a pharmaceutically acceptable salt thereof.

10. A compound of claim 9 wherein R¹ is cyclopropylmethoxy, or a pharmaceutically acceptable salt thereof.

11. A compound of the formula

[structure]

wherein R¹ is (lower)alkoxy, —O—(lower)alkenyl or

—O—(CH₂)ₘ—CH⟨(CH₂)ₙ⟩ in which m is 0 or an integer from 1 to 6 and n is an integer from 2 to 7 and R² is hydrogen, (lower)alkoxy, nitro, amino or di(lower)alkylamino, or a pharmaceutically acceptable salt thereof.

12. A compound of the formula

[structure]

wherein R¹ is methoxy, ethoxy, n-propoxy, isopropoxy, n-butoxy, isobutoxy, sec-butoxy, allyloxy or cyclopropylmethoxy, and R² is methoxy, ethoxy, n-propoxy, isopropoxy, n-butoxy, isobutoxy, sec-butoxy, allyloxy, cyclopropylmethoxy, amino, nitro, or dimethylamino, or a pharmaceutically acceptable salt thereof.

13. A compound of claim 12 wherein R¹ is n-propoxy and R² is methoxy, or a pharmaceutically acceptable salt thereof.

14. A compound of claim 12 wherein R¹ is n-propoxy and R² is amino, or a pharmaceutically acceptable salt thereof.

15. A compound of claim 12 wherein R¹ is n-propoxy and R² is dimethylamino, or a pharmaceutically acceptable salt thereof.

16. A compound of the formula

[structure]

wherein R¹ is halogen, (lower)alkyl, (lower)alkenyl, (lower)alkoxy, —O—(lower)alkenyl,

—O—(CH₂)ₘ—CH⟨(CH₂)ₙ⟩ in which m is 0 or an integer from 1 to 6 and n is an integer from 2 to 7, —OCH₂(CH₂)ₓO(CH₂)ᵧCH₃ in which x is 0 or an integer from 1 to 6 and y is 0 or an integer from 1 to 6, CF₃, —OCF₃, —OCH₂CF₃, hydroxy, (lower)alkylthio, amino,

—N⟨(CH₂)ᵣ⟩ in which r is 4 or 5, (lower)alkylamino, di(lower)alkylamino, carboxyl, —CO₂-(lower)alkyl, —O(CH₂)ᵤCO₂Rᵃ in which u is an integer from 1 to 6 and Rᵃ is hydrogen or (lower)alkyl, Rᶜ—CO— in which Rᶜ is (lower)alkyl, Rᶜ—CO—NH— in which Rᶜ is (lower)alkyl, Rᶜ—COO— in which Rᶜ is (lower)alkyl, $$-O-\overset{O}{\underset{\|}{C}}-NHR^b$$

in which $R^b$ is (lower)alkyl, —O(CH$_2$)$_k$OH in which $k$ is an integer from 2 to 6,

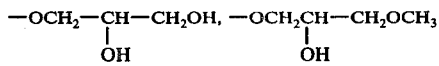

or —OCH$_2$C$_6$H$_5$, or a pharmaceutically acceptable salt thereof.

17. A compound of claim 16 wherein $R^1$ is (lower)alkoxy, —O—(lower)alkenyl,

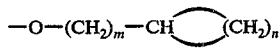

in which $m$ is 0 or an integer from 1 to 6 and $n$ is an integer from 2 to 7, —OCH$_2$(CH$_2$)$_x$O(CH$_2$)$_y$CH$_3$ in which $x$ is 0 or an integer from 1 to 6 and $y$ is 0 or an integer from 1 to 6, —OCF$_3$, —OCH$_2$CF$_3$, hydroxy, (lower)alkylthio, amino, (lower)alkylamino, di(lower)-alkylamino, —O(CH$_2$)$_u$CO$_2$R$^a$ in which $u$ is an integer from 1 to 6 and R$^a$ is hydrogen or (lower)alkyl, —O(CH$_2$)$_k$OH in which $k$ is an integer from 2 to 6,

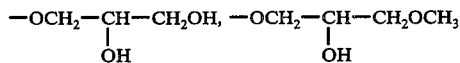

or —OCH$_2$C$_6$H$_5$, or a pharmaceutically acceptable salt thereof.

18. A compound of claim 16 wherein $R^1$ is (lower)alkoxy, —O—(lower)alkenyl,

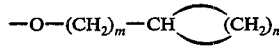

in which $m$ is 0 or an integer from 1 to 6 and $n$ is an integer from 2 to 7, —OCH$_2$(CH$_2$)$_x$O(CH$_2$)$_y$CH$_3$ in which $x$ is 0 or an integer from 1 to 6 and $y$ is 0 or an integer from 1 to 6, —OCF$_3$, —OCH$_2$CF$_3$, hydroxy, —O(CH$_2$)$_u$CO$_2$R$^a$ in which u is an integer from 1 to 6 and R$^a$ is hydrogen or (lower)alkyl, —O(CH$_2$)$_k$OH in which $k$ is an integer from 2 to 6,

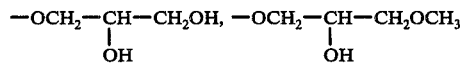

or —OCH$_2$C$_6$H$_5$,
or a pharmaceutically acceptable salt thereof.

19. A compound of claim 16 wherein $R^1$ is (lower)alkoxy, —O—(lower)alkenyl or

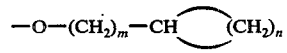

in which $m$ is 0 or an integer from 1 to 6 and $n$ is an integer from 2 to 7, or a pharmaceutically acceptable salt thereof.

20. A compound of claim 19 where $R^1$ is —O—C$_1$—C$_6$ alkyl, —O—C$_2$—C$_6$ alkenyl or

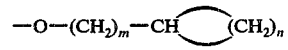

in which $m$ is 0 or an integer from 1 to 4 and $n$ is an integer from 2 to 5, or a pharmaceutically acceptable salt thereof.

21. A compound of claim 20 wherein $R^1$ is methoxy, ethoxy, n-propoxy, isopropoxy, n-butoxy, isobutoxy, sec-butoxy, allyloxy or cyclopropylmethoxy, or a pharmaceutically acceptable salt thereof.

22. A compound of claim 16 wherein $R^1$ is methoxy, or a pharmaceutically acceptable salt thereof.

23. A compound of claim 16 wherein $R^1$ is ethoxy, or a pharmaceutically acceptable salt thereof.

24. A compound of claim 16 wherein $R^1$ is n-propoxy, or a pharmaceutically acceptable salt thereof.

25. The sodium salt of the compound of claim 24.

26. The potassium salt of the compound of claim 24.

27. The ethanolamine salt of the compound of claim 24.

28. The diethanolamine salt of the compound of claim 24.

29. The triethanolamine salt of the compound of claim 24.

30. The ethylenediamine salt of the compound of claim 27.

31. The tris(hydroxymethyl)aminomethane salt of the compound of claim 27.

32. A compound of claim 16 wherein $R^1$ is isopropoxy, or a pharmaceutically acceptable salt thereof.

33. A compound of claim 16 wherein $R^1$ is n-butoxy, or a pharmaceutically acceptable salt thereof.

34. A compound of claim 16 wherein $R^1$ is isobutoxy, or a pharmaceutically acceptable salt thereof.

35. A compound of claim 16 wherein $R^1$ is sec-butoxy, or a pharmaceutically acceptable salt thereof.

36. The (+) optical isomer of the compound of claim 35, or a pharmaceutically acceptable salt thereof.

37. The (−) optical isomer of the compound of claim 35, or pharmaceutically acceptable salt thereof.

38. A compound of claim 16 wherein $R^1$ is allyloxy, or a pharmaceutically acceptable salt thereof.

39. A compound of claim 16 wherein $R^1$ is cyclopropylmethoxy, or a pharmaceutically acceptable salt thereof.

* * * * *

UNITED STATES PATENT AND TRADEMARK OFFICE
CERTIFICATE OF CORRECTION

PATENT NO. : 4,082,751
DATED : April 4, 1978
INVENTOR(S) : Peter F. Juby and Richard A. Partyka It is certified that error appears in the above-identified patent and that said Letters Patent are hereby corrected as shown below:

Claim 1, line 35, "$-O-(CH_2)_m-CH\ (CH_2)_n$" should read -- $-O-(CH_2)_m-CH(CH_2)_n$ --.

Claim 1, line 46, "$-N\ (CH_2)_r$" should read -- $-N(CH_2)_r$ --.

Claim 1, line 51, "$-O(CH_2)u_u$" should read -- $-O(CH_2)_u$ --.

Claim 2, line 20, "$-O-(CH_2)_m-CH\ (CH_2)_n$" should read -- $-O-(CH_2)_m-CH(CH_2)_n$ --.

Claim 2, line 31, "$-N\ (CH_2)_r$" should read -- $-N(CH_2)_r$ --.

Claim 2, line 39, "$R^c-CONH$" should read -- $R^c-COO$ --.

Claim 4, line 4, "$-N(CH_2),$" should read -- $-N(CH_2)_r$ --.

Claim 30, "claim 27" should read -- claim 24 --.

Claim 31, "claim 27" should read -- claim 24 --.

Signed and Sealed this

Fifteenth Day of August 1978

[SEAL]

Attest:

RUTH C. MASON
*Attesting Officer*

DONALD W. BANNER
*Commissioner of Patents and Trademarks*